United States Patent [19]

Remold-O'Donnell

[11] Patent Number: 5,370,991
[45] Date of Patent: Dec. 6, 1994

[54] CLONED GENE ENCODING HUMAN MONOCYTE ELASTASE INHIBITOR

[75] Inventor: Eileen Remold-O'Donnell, Brookline, Mass.

[73] Assignee: The Center for Blood Research, Inc., Boston, Mass.

[21] Appl. No.: 755,461

[22] Filed: Sep. 6, 1991

Related U.S. Application Data

[63] Continuation-in-part of Ser. No. 314,383, Feb. 23, 1989, abandoned.

[51] Int. Cl.$^5$ ............................................. C12Q 1/65
[52] U.S. Cl. .................................. 435/6; 536/23.2; 536/24.3; 536/24.31; 935/78
[58] Field of Search ................ 435/6, 320.1; 536/27, 536/23.2, 24.3, 24.31; 935/78

[56] References Cited

FOREIGN PATENT DOCUMENTS 896543 8/1983 Belgium .
103409 3/1984 European Pat. Off. .
304971 3/1989 European Pat. Off. .

OTHER PUBLICATIONS

Janoff, A., et al., "Proc. Soc. Biol. Med.", 1971, 136:1050–1053.
Blodin, J., et al., "Am. Rev. Resp. Dis.", 1972, 106:477–479.
Dubin, A., "Eur. J. Biochem.", 1977 73:429–435.
Remold-O'Donnell, E., et al., "J. Biol. Chem.", 1983, 258:3251–3257.
Kopitar, M., et al., "Acta Pharm. Jugosl.", 1985, 35:203–212.
Valentine, R., et al., "Proc. Soc. Exp. Biol. Med.", 1981, 168:238–244.
Potempa, J., et al., "J. Biol. Chem.", 1988, 263:7364–7369.
Remold-O'Donnell, E., "J. Exp. Med.", 1985, 162:2142–2155.
Hintz, P., et al., "Biol. Chem. Hoppe-Seyler", 1987, 368:1333–1342 and Biol. Abstracts, vol. 85, No. 3, 1988, Ref. No. 27273.
Remold-O'Donnell, et al. "J. Exp. Med.", 1989, 169:1071–1986.
Welgus, H., et al., "J. Clin. Invest.", 1986, 77:1675–1681.
Senior, R., et al., "J. Clin. Invest.", 1982, 69:384–393.
Sinha, S., "Proc. Natl. Acad. Sci. USA", 1987, 2228–2232.
Takahashi, H., et al., "J. Biol. Chem.", 1988, 263(5):2543–2547.
Suggs, S., et al., "Proc. Natl. Acad. Sci. USA", 1981, 78(11):6613–6617.
Garvey et al., "Methods in Immunology", 3rd Edition, Mar. 1977, pp. 194–231.
Junger, W., et al., "Biol. Chemistry Hoppe-Seyler", 369:63–68, supplement (1988).
Thomas, R., et al., "FASEB Journal", 4:A2156, Abstract No. 2682 (1990).
Takeuchi, K., et al. "J. Biol. Chem.", 264:7431–7436 (1989).
Thomas, R., et al., "J. Leukocyte Biology", 50:568–579 (1991).
DBA Abstract, Accession No. 88-04290, European Patent No. EP 255011, Feb. 3, 1988.
Biosis Abstract, Accession No. 83054104, Von Wilcken-Bergmann et al, EMBO J5(12), 1986, 3219–3226.

Primary Examiner—Amelia Burgess Yarbrough
Attorney, Agent, or Firm—Wolf, Greenfield & Sacks

[57] ABSTRACT

A cloned gene encoding a new human elastase inhibitor is provided. The cloned gene is isolated, purified, and sequenced. The cloned gene encoding a human elastase inhibitor that is substantially non-glycosylated, is capable of forming a covalent complex with elastase and is capable of inhibiting elastase.

2 Claims, 5 Drawing Sheets

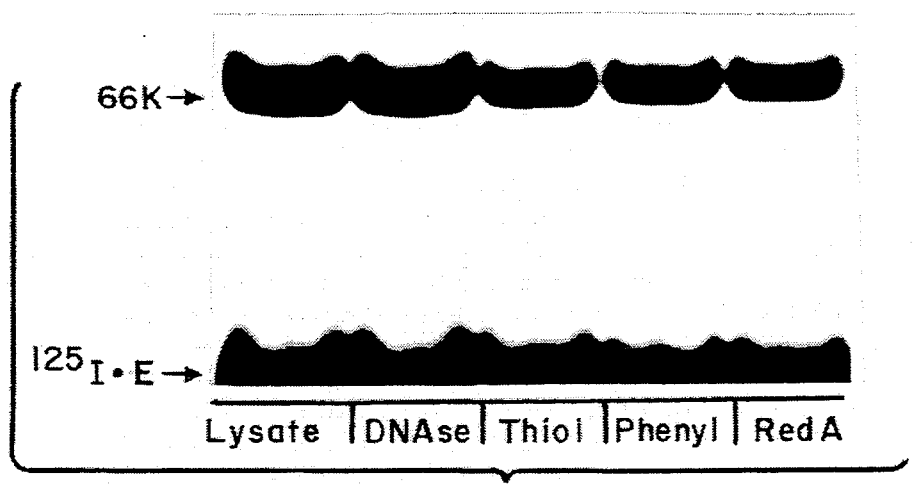
FIG. IA
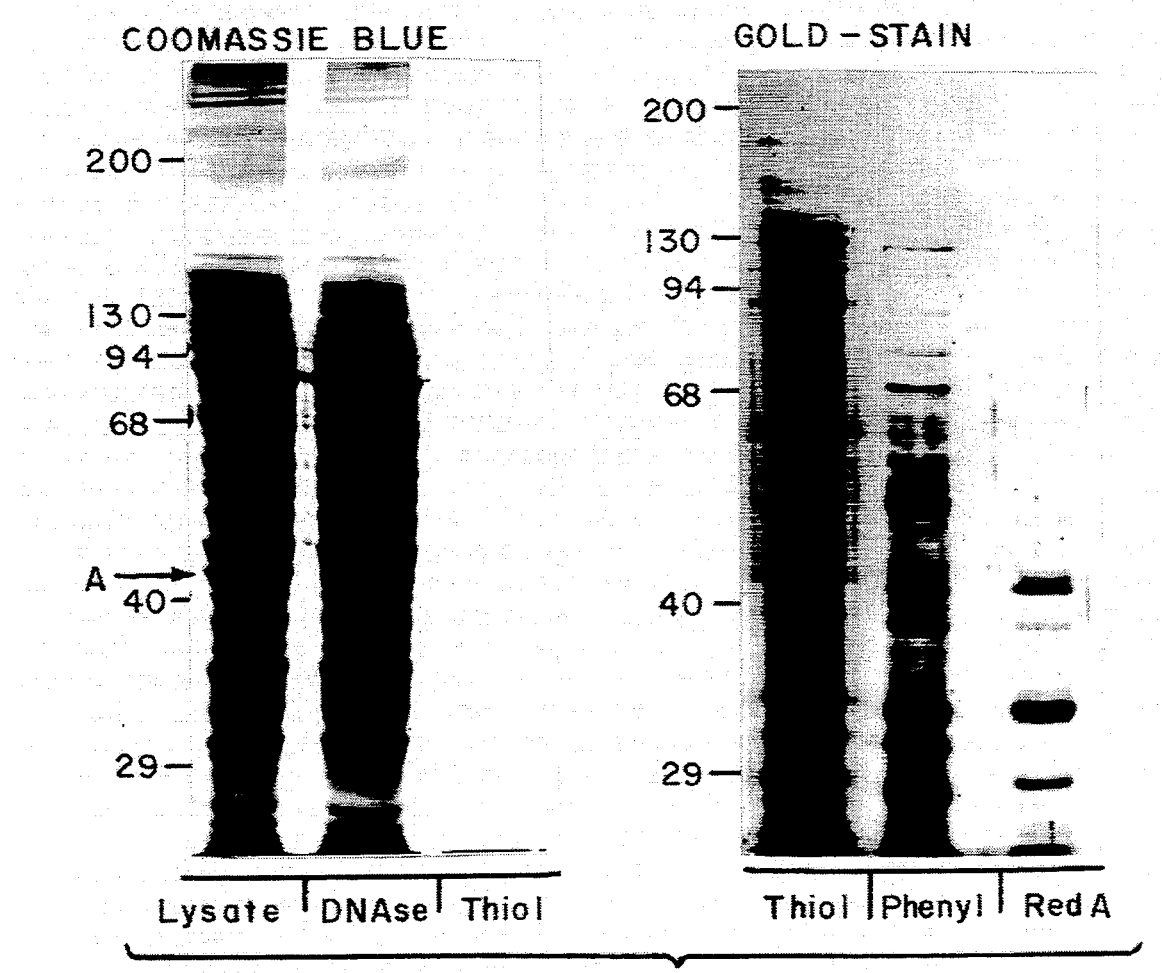
FIG. IB

AMINO ACID COMPOSITIONS

| Residue | No. Residues/100 Amino Acids | | | No. of Residues/Molecule | |
|---|---|---|---|---|---|
| | Avg. of 200 proteins | EI | a1-AT | EI | a1-AT |
| Asx | 10.7 | 11.1 | 10.9 | 40 | 43 |
| Glx | 10.6 | 12.3 | 12.4 | 44 | 50 |
| His | 2.2 | 1.9 | 3.5 | 7 | 13 |
| Lys | 6.5 | 7.1 | 8.6 | 26 | 34 |
| Arg | 4.4 | 3.8 | 1.8 | 14 | 7 |
| Ser | 6.3 | 8.1 | 5.3 | 29 | 21 |
| Thr | 5.7 | 5.7 | 7.6 | 21 | 30 |
| Pro | 4.8 | 5.4 | 4.3 | 20 | 17 |
| Ala | 8.5 | 8.1 | 6.1 | 29 | 24 |
| Cys | 2.3 | 1.5 | 0.2 | 5 | 1 |
| Gly | 8.1 | 7.0 | 5.6 | 25 | 22 |
| Tyr | 3.3 | 2.1 | 1.5 | 8 | 6 |
| Val | 6.8 | 5.2 | 6.1 | 19 | 24 |
| Ile | 5.0 | 3.0 | 4.8 | 11 | 19 |
| Leu | 8.1 | 9.2 | 11.4 | 33 | 45 |
| Phe | 3.7 | 4.9 | 6.8 | 18 | 27 |
| Met | 1.9 | 2.0 | 2.3 | 7 | 9 |
| Trp | 1.3 | ND | 0.5 | ND | 2 |
| Total | | | | .360 | 394 |

FIG. 4

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( v i ) ORIGINAL SOURCE:
    ( G ) CELL TYPE: human histiocytic lymphoma cells
    ( H ) CELL LINE: U937-EI (ATCC #pyright (c) 1990, Microsoft Corp ( x i ) SEQUENCE DESCRIPTION: SEQ ID NO: 1:

Glu Ala Thr Thr Asn Ala Pro Phe Arg
    1      5

( 2 ) INFORMATION FOR SEQ ID NO: 2:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v i ) ORIGINAL SOURCE:
    ( G ) CELL TYPE: human histiocytic lymphoma cells
    ( H ) CELL LINE: U937-EI (ATCC #pyright (c) 1990, Microsoft Corp ( x i ) SEQUENCE DESCRIPTION: SEQ ID NO: 2:

Lys Thr Ile Asn Gln Val Lys
    1     5

( 2 ) INFORMATION FOR SEQ ID NO: 3:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( v i ) ORIGINAL SOURCE:
    ( G ) CELL TYPE: human histiocytic lymphoma cells
    ( H ) CELL LINE: U937-EI (ATCC #pyright (c) 1990, Microsoft Corp (xi) SEQUENCE DESCRIPTION: SEQ ID NO: 3:

```
Phe His Phe Asn Thr Val Glu Glu Val His Ser
 1               5                   10
```

(2) INFORMATION FOR SEQ ID NO: 4:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (vi) ORIGINAL SOURCE:
        (G) CELL TYPE: human histiocytic lymphoma cells
        (H) CELL LINE: U937-EI (ATCC #pyright (c) 1990, Microsoft Corp (xi) SEQUENCE DESCRIPTION: SEQ ID NO: 4:

```
Tyr Gly Ala Asp Leu Ala Ser Val Asp Phe Gln His Ala Ser Glu Asp
 1               5                   10                  15
Ala
```

(2) INFORMATION FOR SEQ ID NO: 5:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vi) ORIGINAL SOURCE:
        (G) CELL TYPE: human histiocytic lymphoma cells
        (H) CELL LINE: U937-EI (ATCC #pyright (c) 1990, Microsoft Corp (xi) SEQUENCE DESCRIPTION: SEQ ID NO: 5:

```
Leu Gly Val Gln Asp Leu Phe Asn Ser
 1               5
```

(2) INFORMATION FOR SEQ ID NO: 6:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (vi) ORIGINAL SOURCE:
        (G) CELL TYPE: human histiocytic lymphoma cells
        (H) CELL LINE: U937-EI (ATCC #pyright (c) 1990, Microsoft Corp (xi) SEQUENCE DESCRIPTION: SEQ ID NO: 6:

```
Pro Glu Asn Leu Asp Phe Ile Glu Val Asn Val Ser Leu Pro
 1               5                   10
```

(2) INFORMATION FOR SEQ ID NO: 7:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (vi) ORIGINAL SOURCE:
        (G) CELL TYPE: human histiocytic lymphoma cells
        (H) CELL LINE: U937-EI (ATCC #pyright (c) 1990, Microsoft Corp (xi) SEQUENCE DESCRIPTION: SEQ ID NO: 7:

```
Tyr Asn Phe Leu Pro Glu Phe Leu Val Ser Thr Gln Lys
 1               5                   10
```

( 2 ) INFORMATION FOR SEQ ID NO: 8:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( v i ) ORIGINAL SOURCE:
        ( G ) CELL TYPE: human histiocytic lymphoma cells
        ( H ) CELL LINE: U937-EI (ATCC #pyright (c) 1990, Microsoft Corp ( x i ) SEQUENCE DESCRIPTION: SEQ ID NO: 8:

```
Val Leu Glu Leu Pro Tyr Gln Gly Glu Glu Leu Ser Met Val Ile Leu
 1               5                  10                  15
Leu Pro Asp Asp Ile Glu
                20
```

( 2 ) INFORMATION FOR SEQ ID NO: 9:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v i ) ORIGINAL SOURCE:
        ( G ) CELL TYPE: human histiocytic lymphoma cells
        ( H ) CELL LINE: U937-EI (ATCC #pyright (c) 1990, Microsoft Corp ( x i ) SEQUENCE DESCRIPTION: SEQ ID NO: 9:

```
Lys Ile Glu Glu Gln Leu Thr Leu Glu Lys
 1               5                  10
```

( 2 ) INFORMATION FOR SEQ ID NO: 10:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( v i ) ORIGINAL SOURCE:
        ( G ) CELL TYPE: human histiocytic lymphoma cells
        ( H ) CELL LINE: U937-EI (ATCC #pyright (c) 1990, Microsoft Corp ( x i ) SEQUENCE DESCRIPTION: SEQ ID NO: 10:

```
Phe Lys Leu Glu Glu Ser Tyr Thr Leu Asn Ser Asp Leu Ala
 1               5                  10
```

( 2 ) INFORMATION FOR SEQ ID NO: 11:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v i ) ORIGINAL SOURCE:
        ( G ) CELL TYPE: human histiocytic lymphoma cells
        ( H ) CELL LINE: U937-EI (ATCC #pyright (c) 1990, Microsoft Corp ( x i ) SEQUENCE DESCRIPTION: SEQ ID NO: 11:

```
Phe Ala Tyr Gly Tyr Ile Glu Asp Leu Lys
 1               5                  10
```

( 2 ) INFORMATION FOR SEQ ID NO: 12:

( i ) SEQUENCE CHARACTERISTICS:
 ( A ) LENGTH: 1316 base pairs
 ( B ) TYPE: nucleic acid
 ( C ) STRANDEDNESS: double standard
 ( D ) TOPOLOGY: linear ( i i ) MOLECULE TYPE: genomic DNA ( i i i ) HYPOTHETICAL: no ( i v ) ANTI-SENSE: no ( x i ) SEQUENCE DESCRIPTION: SEQ ID NO: 12:

```
CCCGCAGCTC GGAGCCCGGA GCGTCCTCGG CGGCTGTCGG TTTTCACC ATG GAG                54
                                                        Met Glu
                                                         1

CAG CTG AGC TCA GCA AAC ACC CGC TTC GCC TTG GAC CTG TTC CTG GCG            102
Gln Leu Ser Ser Ala Asn Thr Arg Phe Ala Leu Asp Leu Phe Leu Ala
         5               10                  15

TTG AGT GAG AAC AAT CCG GCT GGA AAC ATC TTC ATC TCT CCC TTC AGC            150
Leu Ser Glu Asn Asn Pro Ala Gly Asn Ile Phe Ile Ser Pro Phe Ser
     20                  25                  30

ATT TCA TCT GCT ATG GCC ATG GTT TTT CTG GGG ACC AGA GGT AAC ACG            198
Ile Ser Ser Ala Met Ala Met Val Phe Leu Gly Thr Arg Gly Asn Thr
35               40                  45                      50

GCA GCA CAG CTG TCC AAG ACT TTC CAT TTC AAC ACG GTT GAA GAG GTT            246
Ala Ala Gln Leu Ser Lys Thr Phe His Phe Asn Thr Val Glu Glu Val
                 55                  60                  65

CAT TCA AGA TTC CAG AGT CTG AAT GCT GAT ATC AAC AAA CGT GGA GCG            294
His Ser Arg Phe Gln Ser Leu Asn Ala Asp Ile Asn Lys Arg Gly Ala
         70                  75                  80

TCT TAT ATT CTG AAA CTT GCT AAT AGA TTA TAT GGA GAG AAA ACT TAC            342
Ser Tyr Ile Leu Lys Leu Ala Asn Arg Leu Tyr Gly Glu Lys Thr Tyr
         85                  90                  95

AAT TTC CTT CCT GAG TTC TTG GTT TCG ACT CAG AAA ACA TAT GGT GCT            390
Asn Phe Leu Pro Glu Phe Leu Val Ser Thr Gln Lys Thr Tyr Gly Ala
    100                 105                 110

GAC CTG GCC AGT GTG GAT TTT CAG CAT GCC TCT GAA GAT GCA AGG AAG            438
Asp Leu Ala Ser Val Asp Phe Gln His Ala Ser Glu Asp Ala Arg Lys
115                 120                 125                 130

ACC ATA AAC CAG TGG GTC AAA GCA CAG ACA GAA GGA AAA ATT CCG GAA            486
Thr Ile Asn Gln Trp Val Lys Gly Gln Thr Glu Gly Lys Ile Pro Glu
                135                 140                 145

CTG TTG GTC TCG GGC ATG GTT GAT AAC ATG ACC AAA CTT GTG CTA GTA            534
Leu Leu Val Ser Gly Met Val Asp Asn Met Thr Lys Leu Val Leu Val
            150                 155                 160

AAT GCC ATC TAT TTC AAG GGA AAC TGG AAG GAT AAA TTC ATG AAA GAA            582
Asn Ala Ile Tyr Phe Lys Gly Asn Trp Lys Asp Lys Phe Met Lys Glu
        165                 170                 175

GCC ACG ACG AAT GCA CCA TTC AGA TTG AAT AAG AAA GAC AGA AAA ACT            630
Ala Thr Thr Asn Ala Pro Phe Arg Leu Asn Lys Lys Asp Arg Lys Thr
    180                 185                 190

GTG AAA ATG ATG TAT CAG AAG AAA AAA TTT GCA TAT GGC TAC ATC GAG            678
Val Lys Met Met Tyr Gln Lys Lys Lys Phe Ala Tyr Gly Tyr Ile Glu
195                 200                 205                 210

GAC CTT AAG TGC CGT GTG CTG GAA CTG CCT TAC CAA GGC GAG GAG CTC            726
Asp Leu Lys Cys Arg Val Leu Glu Leu Pro Tyr Gln Gly Glu Glu Leu
                215                 220                 225

AGC ATG GTC ATC CTG CTG CCG GAT GAC ATT GAG GAC GAG TCC ACG GGC            774
Ser Met Val Ile Leu Leu Pro Asp Asp Ile Glu Asp Glu Ser Thr Gly
            230                 235                 240

CTG AAG AAG ATT GAG GAA CAG TTG ACT TTG GAA AAG TTG CAT GAG TGG            822
Leu Lys Lys Ile Glu Glu Gln Leu Thr Leu Glu Lys Leu His Glu Trp
```

```
                245                         250                         255
    ACT AAA CCT GAG AAT CTC GAT TTC ATT GAA GTT AAT GTC AGC TTG CCC        870
    Thr Lys Pro Glu Asn Leu Asp Phe Ile Glu Val Asn Val Ser Leu Pro
        260                     265                 270

AGG TTC AAA CTG GAA GAG AGT TAC ACT CTC AAC TCC GAC CTC GCC CGC        918
    Arg Phe Lys Leu Glu Glu Ser Tyr Thr Leu Asn Ser Asp Leu Ala Arg
    275                 280                     285                 290

CTA GGT GTG CAG GAT CTC TTT AAC AGT AGC AAG GCT GAT CTG TCT GGC        966
    Leu Gly Val Gln Asp Leu Phe Asn Ser Ser Lys Ala Asp Leu Ser Gly
                    295                 300                 305

ATG TCA GGA GCC AGA GAT ATT TTT ATA TCA AAA ATT GTC CAC AAG TCA       1014
    Met Ser Gly Ala Arg Asp Ile Phe Ile Ser Lys Ile Val His Lys Ser
                310                 315                 320

TTT GTG GAA GTG AAT GAA GAG GGA ACA GAG GCG GCA GCT GCC ACA GCA       1062
    Phe Val Glu Val Asn Glu Glu Gly Thr Glu Ala Ala Ala Ala Thr Ala
            325                 330                 335

GGC ATC GCA ACT TTC TGC ATG TTG ATG CCC GAA GAA AAT TTC ACT GCC       1100
    Gly Ile Ala Thr Phe Cys Met Leu Met Pro Glu Glu Asn Phe Thr Ala
            340                 345                 350

GAC CAT CCA TTC CTT TTC TTT ATT CGG CAT AAT TCC TCA GGT AGC ATC       1158
    Asp His Pro Phe Leu Phe Phe Ile Arg His Asn Ser Ser Gly Ser Ile
    355                 360                 365                 370

CTA TTC TTG GGG AGA TTT TCT TCC CCT TAGAAGAAAG AGACTGTAGC             1205
    Leu Phe Leu Gly Arg Phe Ser Ser Pro
                    375

AATACAAAAA TCAAGCTTAG TGCTTTATTA CCTGAGTTTT TAATAGAGCC                1255

AATATGTCTT ATATCTTTAC CAATAAAACC ACTGTCCAGA AAMAAAAAAA                1305

AAAAAAAAAA A                                                          1316
```

CLONED GENE ENCODING HUMAN MONOCYTE ELASTASE INHIBITOR

GOVERNMENT SUPPORT

The invention described herein was supported in part by grants AI-20185 and HL-41579 from the National Institutes of Health

RELATED APPLICATIONS

The present application is a continuation in part of application Ser. No. 07/314,383, filed Feb. 23, 1989 (now abandoned), the entire contents of which are incorporated herein by reference.

BACKGROUND OF THE INVENTION

This invention relates in general to molecular biology, pharmacology and medicine and in particular to the isolation, purification and cloning of a human proteinase inhibitor.

Preservation of the integrity of local organ function requires a delicate balance of the activities of phagocytic cell proteinases and the action of proteinase inhibitors. Loss of this balance is believed to be a major causative factor in the pathogenesis of asthma, chronic bronchitis, cystic fibrosis, emphysema, sarcoidosis, respiratory distress syndromes, arthritis, and certain skin diseases and possibly malignancies. For example, excess release of elastase by neutrophils and monocytes as well as excess accumulation of monocytes and neutrophils are believed responsible for tissue injury in inflamatory conditions such as arthritis and emphysema and in neutrophil mediated injury to endothelial cells. To acquire the ability to monitor and manipulate the proteinase-proteinase inhibitor balance requires that the relevant molecules be identified, isolated and purified.

Of the phagocytic cell proteinases, an important one is the serine active site proteinase that is commonly called "neutrophil elastase". Human neutrophil elastase is a 218 amino acid glycosylated protein of known sequence that is particularly abundant in neutrophils (0.5% of total protein) and is also found in monocytes and macrophages. Elastase cleaves extracellular matrix proteins such as elastin, proteoglycans, fibronectin, type III and type IV collagen, and certain soluble proteins. It also is required by neutrophils for their migration through cell barriers in vitro.

The continuous action of elastase inhibitors in vivo is evident from the neutrophil turnover rate. Despite the fact that neutrophils enter most body sites, turnover of about $10^{11}$ neutrophils with a content of about 50 mg elastase occurs daily in humans without evidence of uncontrolled tissue degradation.

A prevalent soluble blood protein, αl-antitrypsin (αl-AT), is a fast-acting elastase inhibitor in vitro. Individuals with genetically reduced levels of El-AT (homozygous Z-variant) are predisposed to develop pulmonary emphysema in the third or fourth decade of life due to uncontrolled elastase action. Human αl-AT currently is used to treat congenital αl-AT deficiency.

Molecules differing from αl-AT that fulfill the requirements of a physiological regulator of neutrophil elastase activity have been detected in monocytes and neutrophils in several species. It was reported in 1971 that an endogenous elastase inhibitor with properties of a protein was detected in the cytosolic fraction of human blood leukocytes and human lung macrophages (1,2). Cytosolic proteins that inhibit elastase were identified and purified from horse blood neutrophils (3,4), pig blood leukocytes (5) and bovine lung macrophages (6). An elastase inhibitor in the extracellular fluid of cultured guinea pig macrophages has been identified by its ability to form a covalent complex with elastase (7). Larger quantities of the guinea pig elastase inhibitor have been found in macrophage lysates (7). More recently, a prevalent, fast-acting endogenous elastase inhibitor protein has been detected in mature human monocytes and monocyte-like cells (8). To date, no one has been able to isolate, purify, characterize and clone this human elastase inhibitor.

SUMMARY OF THE INVENTION

According to the invention, Human Elastase Inhibitor (Human EI) is isolated, purified, cloned and characterized at the molecular level. Human EI is nonglycosylated, forms a covalent complex with elastase and inhibits the elastinolytic activity of elastase. The molecule appears to have a cysteine residue essential for interaction with elastase, since the treatment of Human EI with iodoacetamide is capable of preventing Human EI from forming a complex with elastase. Human EI is stable to reducing agents; purified Human EI appears to have a blocked amino-terminus. Human EI has a molecular weight of about 42,000.

Human EI has been digested, purified and partially sequenced and includes Sequence I.D. Numbers 1-11. Human EI has also been cloned by recombinant DNA techniques and sequenced.

In addition to purified or substantially purified Human EI, the invention also provides recombinantly derived Human EI, and derivatives, variations, and portions of Human EI.

A human cDNA library from monocytes or monocyte-like cells was expressed in suitable host cells using conventional expression vectors to yield colonies, each colony expressing a different portion of the cDNA library. Then, the colonies were screened using an oligonucleotide encoding at least a portion of one of the foregoing protein sequence I.D. Numbers to identify colonies containing portions of the cDNA for Human EI.

The recombinant expression vectors then were isolated from the selected colonies. The vectors each contain a portion of the cDNA sequence for human EI. These sequences were excised and sequenced. By identifying overlapping sequences in the DNA fragments corresponding to portions of the cDNA for human EI, the DNA sequence for the human elastase inhibitor was obtained. Unique restriction sites were identified Ln the cDNA for human EI, thereby providing a convenient mechanism for insertion of the cDNA into a suitable expression system.

The expressed molecule may be selected from the group consisting of:

(1) Human EI;

(2) variations, portions or derivatives of Human EI; and (3) molecules including any one of amino acid sequence I.D. Numbers 1-11.

Substantially pure preparations of oligonucleotides encoding Human EI, or variations, derivatives or portions thereof also are provided (sequence I.D. Number 12). These oligonucleotides may be the product of natural, synthetic or recombinant methods. In addition, sense or antisense DNA or RNA corresponding to the disclosed oligonucleotides are provided. Likewise, preparation of antibodies with selective specificity for or capable of binding with Human EI, its variants, derivatives or portions are also provided.

The invention also provides for a method of producing functional variations of the Human EI protein. The method includes providing a modified DNA sequence encoding for human EI or at least one functional variation thereof, inserting the modified DNA sequence into a suitable expression system (e.g., vector and host); expressing modified human EI; and testing the ability of the modified human EI to bind with elastase and/or other proteases.

The Human EI, antibodies to Human EI and oligonucleotides and vectors encoding Human EI and variations, derivatives or portions thereof may be used alone or coupled with other moieties to treat various medical conditions and/or as diagnostic tools in determining the existence and degree of such conditions.

BRIEF DESCRIPTION OF THE DRAWINGS

FIG. 1 is an autoradiograph showing the presence of Human EI at certain steps during purification;

FIG. 4 shows the amino acid composition of pure EI as compared to that of αl-AT, wherein the mean amino acid composition of >200 proteins is from Reeck, G. R., Fisher, L. "A Statistical Analysis of the Amino Acid Compositions of Proteins." *Int. J. Peptide Protein Res.*, 1973, 5:109–117; EI values are means of data from three preparations. Number of residues per molecule EI were calculated based on Mr=42,000; and α-1AT composition is calculated form Carrell, R.W., Jeppsson, J-O., Laurell, C-B., Brennan, S. O., Owen, M. C., Vaughan, L., Boswell, D. R., "Structure and Variation of Human αl-Antitrypsin." Nature, 1982, 298:329–3334 (N.D.=not determined).

DETAILED DESCRIPTION OF THE INVENTION

Figure 2:
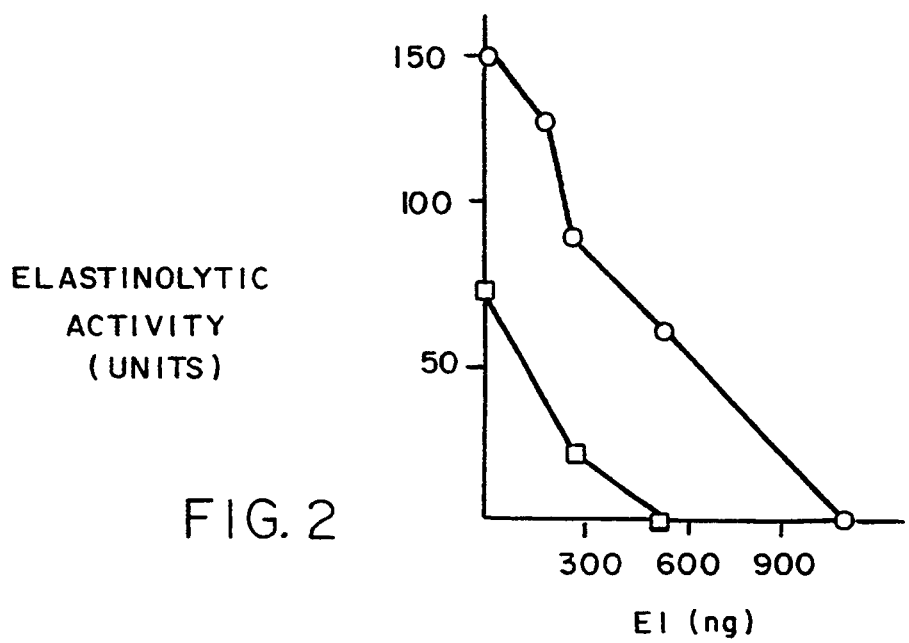
FIG. 2 is a graph showing dose-dependent inhibition of elastinolysis caused by Human EI

Human EI is a fast acting, cell-associated, essentially irreversible inhibitor of porcine pancreatic elastase and human neutrophil elastase, both serine active-site protein elastases (hereinafter "elastase"). It is found at high levels in neutrophils, monocytes and macrophages. Human EI reacts quantitatively with elastase to form an EI-elastase complex and to inhibit the elastinolytic activity of elastase. The complex is stable in boiling SDS (sodium dodecyl sulfate), indicating a covalent bond between the EI and the elastase.

Based on functional criteria, Human EI may be grouped with the serine proteinase inhibitors of the Serpin family. Human EI does not react with elastase that has been inactivated with the serine active site reagent DFP (diisopropyl fluorophosphate). The covalent complex is stable in boiling SDS and also is susceptible to base-catalyzed cleavage. These mechanisms of action are characteristic of serine proteinase inhibitors of the Serpin family. However, Human EI differs from other serine proteinase inhibitors in that the treatment of Human EI with iodoacetamide abrogates its ability to form a complex with elastase, indicating an essential cysteine residue. Human EI also differs from all other molecules based on searches of databases for the amino acid sequence derived from the cDNA encoding human EI.

Human EI is a single polypeptide having a molecular weight of about 42,000. The negligble levels of carbohydrate detected on gas-liquid chromatography and the insensitivity of Human EI to treatment with the glycosidase PNGase F (peptide:N-glycosidase F) indicate that Human EI is non-glycosylated. The amino-terminus of purified Human EI appears to be blocked.

Pure Human EI was purified and partially sequenced Human EI includes Sequence I.D. Numbers 1 through 11.

Purification of Human EI

A series of steps were involved in the purification of Human EI. The presence of Human EI was confirmed at each step by the ability of a sample taken at each step to form a covalent complex with $^{125}$I-elastase. (7,8) The details of the confirmation procedure are set forth in the foregoing references, the disclosures of which are incorporated herein. In general, fractions suspected of containing Human EI were incubated at 37° C. for 10 minutes with 30–200 ng of $^{125}$I-labeled porcine pancreatic elastase (Elastin Products, Pacific, MO.) The covalent EI-elastase complex was detected by autoradiography after SDS polyacrylamide slab gel-electrophoresis using the Fairbanks/Laemmli gel system. This system employs relatively low pH and low primary amine concentration to minimize hydrolysis of the complex during electrophoresis (8).

Obtaining Cell Lysates

U937 cells were used as the source of Human EI. U937 cells are human histiocytic lymphoma cells (9). The particular U937 cells used are believed to be a subline at a slightly more advanced stage of differentiation than U937 as originally characterized (9). The cell line used is hereafter referred to as U937-EI. This cell line has been deposited at the ATCC, Rockville, Md., under Accession Number CRL 10026.

U937-EI cells were grown in RPMI 1640 medium or Dulbecco's modified Eagles medium with 4.5 mg/ml glucose, 10% FCS and 50 micrograms per ml gentamycin. The U937-EI cells from 12 liter cultures (approximately $1.8 \times 10^{10}$ cells) grown by the Massachusetts Institute of Technology Cell Culture Center were washed twice by pelleting at 4° C. in Ca++/Mg++ containing PBS. The cells at $2 \times 10^7$ per ml in HBSS (Hanks' Balanced Salt Solution) were incubated at about 22° C. for 15 minutes to remove adsorbed αl-AT (8). The cells were brought to 4° C. and pelleted. Lysates ($2.5 \times 10^7$ cells per ml) were prepared by extracting the cells with 0.5% NP-40 (Nonidet P-40 [NP-40] is a nonionic detergent marketed in the United States by Gallard Schlesinger, Carle Place, N.Y. The material is an octyl phenol ethylene oxide condensate with 9 moles ethylene oxide. It is a product of BDH Limited, Poole, England; BDH obtains the material from Shell Chemical Co., England) ill PBS for 4 minutes at about 22° C. and 10 minutes at 4° C., and clarified by centrifugation in a Sorvall SS34 rotor (Dupont Co., Wilmington, Del.) at 18,000 rpm for 30 minutes at 4° C.

Separation of Actin on DNAse-Sepharpose

In preliminary purification experiments, EI activity was lost concomittant with the formation of actin (10) containing precipitates. To avoid this loss, the cell lysates were immediately chromatographed on DNAse-Sepharose, which specifically absorbs actin.

The DNAse Sepharose affinity resin was prepared as follows: Deoxyribonuclease I (bovine pancreas; 1800 Kunitz units/mg protein; Sigma Chemical Co., St. Louis, MO) was treated with 2 mM diisopropyl-fluorophosphate (DFP) in PBS for 30 min at 22° C., and was coupled at 3 mg/ml in 0.1M NaHCO$_3$, pH 8.5 to activated Sepharose by mixing for 18 hr at 4° C. (greater than 90% coupling efficiency). The activated Sepharose was either Activated Sepharose 4B supplied as an activated lyophilized powder by Pharmacia Fine Chemical (now Pharmacia LKB Biotechnology, Inc., Piscataway, N.J.), which was reconstituted and prepared for coupling following the manufacturer's suggestion (i.e., reconstituted with 1 mM HCl and washed with 1 mM HCl at 22° C. for 15 min. followed by washing with coupling buffer) or Sepharose 6B activated immediately before coupling (P. Cuatrecasas, "Protein Purification by Affinity Chromatography: Derivatives of Agarose and Polyacrylamide Beads", *J. Biol. Chem.*, 1970, 245:3509–3065) by treatment with CNBr (2.3 g per 100 ml Sepharose) at pH 11 and ~22° C. for 10 min. The resin was treated at 22° C. once with 10 mM Tris-HCl buffer, pH 8.0 for 2 hr; three cycles with 100 mM sodium acetate buffer pH 4.0 followed by 100 mM NaHCO$_3$ pH 8.5; once with PBS; and once with 2 mM DFP in PBS for 30 min. The resin was stored in PBS with 0.02% sodium azide at 4° C. and was equilibrated with PBS immediately before use.

The cell lysate (~720 ml) was incubated with 180 ml DNAse-Sepharose for 30 minutes at 4° C. in a roller bottle. The mixture was transferred to a 6.5 cm diameter column, and the nonadherent fraction, together with a 0.8 column volume wash with 0.5% NP-40 in PBS was stored at −70° C. The presence of Human EI in the nonadherent fraction was measured as set forth above. As shown in FIG. 1, a protein in the nonadherent fraction combined with elastase to form the $^{125}$I-elastase - elastase inhibitor complex of apparant molecular weight 66,000.

Thiopropyl-Sepharose-6B Separation.

Thiopropyl-Sepharose 6B is a mixed disulfide affinity resin supplied by Pharmacia Fine Chemicals. It contains approximately 20 μ moles per ml swollen gel of 2-thiopyridyl residues in mixed disulfide linkage to hydroxpropyl residues; the latter residues are linked to the Sepharose 6B matrix via ether linkage. Thiopropyl-Sepharose 6B is synthesized by a method such as that described by R. Axen, Drevin, H. and Carlsson, J. (Preparation of modified agarose gels containing thiol groups, *Acta Chem. Scand. B*, 1975, 29, 471–474). Human EI adheres to Thiopropyl-Sepharose-6B, while most proteins do not. The Thiopropyl-Sepharose-6B was equilibrated against 0.5% NP-40, 10 mM Tris-HCl buffer, pH 7.4, 150 mM NaCl, 1 mM EDTA (NP-40/Tris/150-NaCl/EDTA) at 22° C. for 30 min. The DNAse-nonadherent fraction (~900 ml) then was incubated with occasional stirring at 22° C. with 30 ml of the Thiopropyl-Sepharose-6B. The mixture was transferred to a 3 cm column and washed sequentially with one column volume of NP-40/Tris/150-NaCl/EDTA, NP-40/Tris/500-NaCl, Tris/500-NaCl, and Tris/150-NaCl. The column was eluted with 50 mM mercaptoethanol in Tris/150-NaCl to yield a single 70 ml "Thiol eluate" fraction. Again, the presence of Human EI was confirmed as set forth above. As shown in FIG. 1, a protein in the Thiol eluate fraction combined with elastase to form the $^{125}$I-elastase - elastase inhibitor complex.

Phenyl-Sepharose-CL4B Separation.

Sepharose is the registered trademark for spherical agarose gel beads manufactured by Pharmacia Fine Chemicals. Sepharose 6B, ~6% agarose, consists of 40–210 micron particles; Sepharose 4B, ~4% agarose, consists of ~40–190 micron particles. The agarose used to manufacture Sepharose is produced from selected agar (Hjerten, S., "A New Method for Preparation of Agarose for Gel Electropheresis". *Biochim. Biophys. Acta* 1962, 62:445–449 and S. Hjerten, Chromatography on agarose spheres, in "Methods in Immunology and Immunochemistry", Ed: M. W. Chase and C. A. Williams, Academic Press, Inc., N.Y., 1968, pages 149–154).

Phenyl-Sepharose-CL4B is a derivative of Sepharose CL-4B; the latter is prepared by crosslinking the agarose with 2,3-dibromopropanol (patented, UK Patent I 352 613 and corresponding patents in other countries) and desulphating the resulting gel by alkaline hydrolysis under reducing conditions (J. Porath, Janson, J-C, Laas, T., "Agar derivatives for chromatography, electrophoresis and gel-bound enzymes. I. Desulphated and reduced crosslinked agar and agarose in spherical bead form". *J. Chromatogr.*, 1971, 60:167–177). The phenyl groups are introduced by reaction of Sepharose CL-4B with the glycidyl ether (S. Hjerten, Rosengren, J., and Pahlman, S., "Hydrophobic interaction chromatography. The synthesis and the use of some alkyl and aryl derivatives of agarose." *Chromatogr.*, 1974, 101, 281–288) to produce a derivative with the phenyl group attached to the monosaccharide unit of the agarose matrix via ether linkage. The concentration of coupled phenol ligand is approximately 40 μmoles/ml swollen gel.

The EI active fraction of the Thiol-eluate was applied at approximately 22° C. to a 3.5 cm column of Phenyl-Sepharose-CL4B (70 ml; Pharmacia) equilibrated against 10 mM Tris-HCl buffer, PH 7.4, 150 mM NaCl, 1 mM mercaptoethanol (Tris/150-NaCl/ME). Phenyl-Sepharose-CL4B separates proteins based on differences in their hydrophobicity. The nonadherent fraction was collected, together 20 ml (approximately) wash using Tris/150-NaCl/ME. The presence of Human EI in the nonadherent fraction was confirmed as set forth above (FIG. 1).

Matrix gel Red A separation.

Matrix gel Red A is a "group selective" affinity resin marketed by Amicon Corp., Lexington, Mass. It consists of crosslinked 5% agarose with 3–5 mg of covalently coupled dye per ml swollen gel. The dye is known as red A, reactive red 120 and Procion Red HE3B, a registered trademark of Imperial Chemical Industries (Baird, J., Sherwood, R., Carr, R. and Atkinson, A., "Enzyme Purification by Substrate Elution Chromatography from Procion Dye-Polysaccharide Matrices.", *FEBS Lett.*, 70: 61).

The Phenyl- nonadherent fraction (approximately 110 ml) was diluted with 0.5 volume Tris/ME and applied at 4° C. to a 2 cm diameter column of 20 ml Matrix gel Red A equilibrated against Tris/100-NaCl/ME. Matrix gel Red A separates proteins based on their ability to bind to the Red A dye. The nonadherent fraction, including one column volume wash with Tris/100-NaCl/ME, was collected, tested for the presence of Human EI (FIG. 1), dialyzed against Tris/50-NaCl/ME for 3 hr at 4° C., and stored at −70° C.

HPLC DEAE-5PW Separation.

DEAE-5PW is a weak anion exchange resin for high performance liquid chromatography (HPLC) that separates proteins based on small differences in charge properties. DEAE-5PW is prepared by introducing diethylaminoethyl (DEAE) groups onto a hydrophilic rigid resin; it is a product of Waters Division, Millipore Corp., Milford, Mass.), and is also known as Protein-Pak DEAE-5PW; (Protein-Pak is a tradename for various Waters resins). There is 0.1 micromole of effective DEAE groups per ml of resin. DEAE-5PW is a 10 micron spherical diethylaminoethyl functionalized polymethacrylate resin having 1000 angstrom pores. The resin is encased in a 7.5×75 mm 316 stainless steel column.

Portions (50 ml) of the dialyzed Red A-nonadherent fraction were filtered through 0.2 μm nylon membranes (Schleicher and Schuell, Keene, NH) and applied at 0.8 ml/min to the DEAE-5PW column equilibrated against Tris/D0-NaCl/ME at 22° C. The column was washeed with equilibration buffer. To elute Human EI, Tris/85-NaCl/ME was applied, and fractions absorbing at 280 nm were collected and assayed for the presence of Human EI as set forth above.

To concentrate EI, active fractions from 3–4 DEAE-fractionations were pooled, diluted with Tris/ME, and reapplied to the DEAE-5PW column in Tris/50-NaCl/ME. A single EI-containing fraction of 1 to 2.5 ml was eluted with Tris/140-NaCl/ME. The presence of Human EI was confirmed as above. This fraction is 85–95% pure Human EI as indicated by gold-stained SDS electrophoresis gels, and since it is active and concentrated (e.g., 0.4 mg/ml), this preparation of Human EI is preferred for activity studies and functional studies.

HPLC-Gel Filtration Chromatography.

For some applications, the remaining contaminants were removed by HPLC gel filtration chromatography using the HPLC gel filtration resin Protein-Pak I-125. Protein-Pak I-125a product of Waters Division, is a 10 micron diol-bonded silica gel with a 100 Angstrom pore size. It consists of irregular silica particles covalently bonded with a dihydroxyalkyl silane to generate a hydrophilic material that is non-absorptive toward proteins and suitable for gel filtration chromatography. It is supplied encased in 7.8×30 mm columns of 316 stainless steel.

Portions of pooled concentrated Human EI from DEAE-5PW (200–1000 μl ) were gel-filtered at 1.0 ml/min on two Protein-Pak I-125 columns in series totaling 7.8×600 mm equilibrated against 10 mM Tris HCl buffer, pH 7.4, 90 mM NaCl. Fractions absorbing at 214 nm (two peaks) were collected, and, after addition of mercaptoethanol to 1 mM, were assayed for content of Human EI as set forth above. The pooled active peak (second peak) represents pure or substantially pure Human EI. Alternatively, the HPLC gel filtration was carried out using 50 mM $NH_4HCO_3$ as the buffer and the buffer was removed by lyophilization from the pooled fraction containing Human EI.

Fractions from the purification were analyzed by Laemmli SDS-electrophoresis as described (8). The polypeptides were gold stained after transfer to PVDF membranes (polyvinylidine difluoride; 0.45 μm; Millipore Corp., Bedford, Mass.) (constant 70 mAmps; 160 v/1.6 A power supply; Bio-Rad Laboratories, Richmond, Calif.) with 42 mM Tris/190 mM glycine buffer, pH 8.3 for 18 hr at ~22° C. (Transphor Cell Hoefer Scientific, San Francisco, Calif.). The PVDF membranes were washed seven times with 0.1% Tween-20 (Tween 20 is a registered trademark of ICI Americas for a polyethoxyethanol sorbitan; the product was obtained as a 10% aqueous solution packed in glass ampules under nitrogen from Pierce Co., Rockford, Ill. under the name Surfact-Amp 20) in PBS (2×15 min; 5×5 min) and twice with water, and were incubated with 0.2–0.3 ml/cm² of AuroDye protein stain (Janssen Pharmaceutica, Piscataway, N.J.) at ~22° C. for ≥4 hr. AuroDye is a stabilized colloidal gold sol (20 nm) adjusted to approximately pH 3 which stains proteins dark red.

Determination of molecular weight of EI.

The apparent molecular weight of Human EI was determined as 42,000 by comparing its mobility on SDS electrophoresis gels (11) with that of previously described (8) pure proteins of known molecular weight; the proteins were detected by gold staining of electrophoretic transfers.

Inhibition of Elastinolysis.

Human EI was assayed for elastinolytic activity by generation of a lytic zone in an elastin-containing agar gel (12). Generally, varying amounts of Human EI (pooled, concentrated DEAE fraction) were combined with either 75 ng or 150 ng pancreatic elastase for five minutes at about 22° C., and then were incubated in wells of fluorescein-elastin-agar plates for 48 hours at 37° C. The extent of elastinolysis, measured as the diameter of the lysis rings (average of duplicate determinations), was converted to units (one unit equaling the activity of one ng elastase) by reference to a parallel standard curve. Tests were run using 75 ng of elastase (boxes) and 150 ng of elastase (circles). Human EI caused dose-dependent inhibition of elastinolysis by elastase, thereby demonstrating that Human EI inhibits elastase (FIG. 2).

Figure 3:
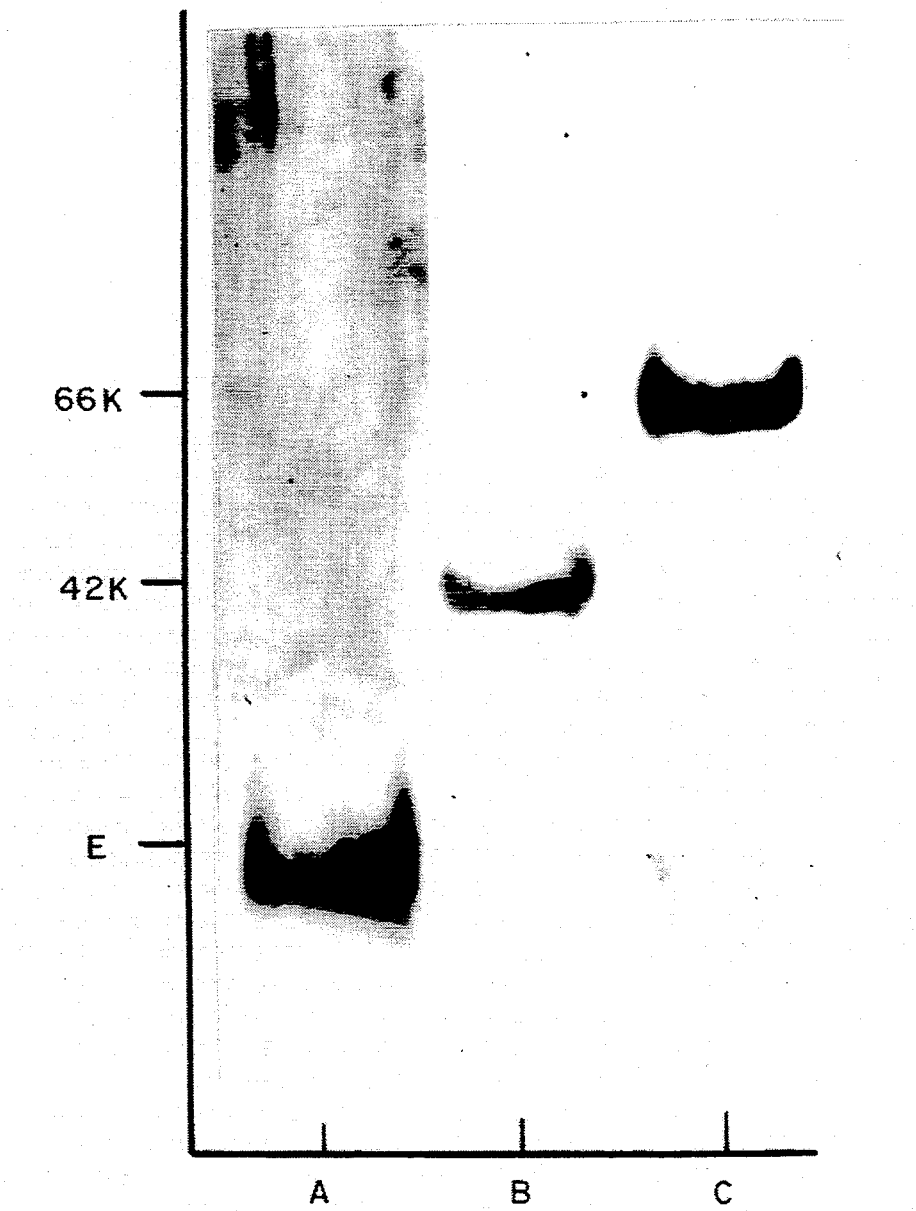
FIG. 3 is an autoradiograph showing Human EI and Human EI complexed with elastase.

To demonstrate that the $M_r$ 42,000 polypeptide is the elastase inhibitor, the DEAE-purified fraction was incubated with nonlabeled elastase and examined on silver-stained (13) SDS-electrophoresis gels. The SDS gel included three lanes, one for EI, one for elastase and one for a mixture of the EI and elastase. On co-incubation for 1 min, the $M_r$ 42,000 polypeptide and elastase disappeared concomitant with the formation of a $M_r$ 66,000 elastase-elastase inhibitor complex (FIG. 3). This finding demonstrates that the $M_r$ 42,000 polypeptide is the elastase inhibitor. It also shows that the bulk of the purified molecules have retained complex-forming activity and that the reaction of the purified molecule with elastase is rapid (complete at 1 min). The molecular weights of the reactants and the complex clearly suggest that the reaction has 1:1 stoichiometry.

Amino Acid Composition.

An aliquot of lyophilized pure Human EI was hydrolyzed in 6 N HCl at 110° C. for 24 hours and the amino acid composition was determined on a Dionex D-500 Analyzer. The content of Cys/2 (cysteine plus ½ cystine) was determined as cysteic acid after performic acid oxidation (14). The amino acid composition of the sample is presented in FIG. 4, together with the mean composition of 200 purified proteins and that of αl-AT, the known elastase inhibitor found in plasma.

Carbohydrate composiiton.

The carbohydrate content of pure Human EI was determined by methanolysis of a lyophilized sample by gas-liquid chromatography after conversion to the per(-trimethylysilyl) derivatives (15). Per molecule of EI, 3.6 residues of xylose (believed to be a contaminant) and 0.5 residue of mannose (average values for two preparations) were detected. Galactose, N-acetylglucosamine, N-acetylgalactosamine, and sialic acid were not detected. Pure Human EI also was treated with the glycosidase PNGase F, which cleaves all classes of N-linked carbohydrate units (16). On treatment with 140-4200 mU/ml PNGase F, no change was detected in the apparent molecular weight of EI. The foregoing indicates that pure Human EI is a non-glycosylated protein.

Amino Acid Sequencing.

Two attempts to determine amino terminal sequence of pure Human EI yielded no sequence, suggesting that the amino-terminus is blocked. Therefore, it was decided to cleave the protein in order to determine amino acid sequence. Preparations of Human EI, between 40 μg and 80 μg, were examined, and treated with the proteinase trypsin. Because of the possibility that Human EI would inhibit trypsin, the human EI protein was heat-treated (85°-90° C. for 8 min) to destroy its inhibitory activity. The heat-treated protein was incubated with 0.3%-1% (wt/wt) L-1-tosylamido-2-phenylethylchloromethylketone-treated trypsin (Sigma Chemical Co., St. Louis, Mo.) at pH 8.0 and at 37° C. for 18 hr, conditions that were established in small-scale preliminary experiments. A small portion of the tlrypsin-treated preparation was analyzed by SDS-electrophoresis and gold-staining to insure that degradation of Human EI was complete.

The resulting tryptic peptides were fractionated by chromatography on a $C_{18}$ reverse phase HPLC column with a 2-75% acetonitrile gradient in 0.1% trifluoroacetic acid in water. The $C_{18}$ column is a 300 Angstrom pore size silica with a bonded phase with 5 micron particle size encased in a stainless steel column of 0.46-25 cm, from the Vydac Division (The Separations Groups, Hesperia, Calif.). The column is designed for reverse phase HPLC chromatography of proteins and peptides. Fractions containing the separated peptide peaks were collected based on absorption at 214 nm; and solvent was removed by lyophilization. The peptide peaks were subjected to amino terminal amino acid sequencing on a gas phase protein sequencer (ABI 470A, Applied Biosystems, Foster City, Calif.) equipped with an on-line phenylthiohydantoin HPLC analyzer (ABI 120A On-line PTH analyzer).

Partial amino acid sequences, totalling 137 amino acid residues, were established by sequencing eleven peptides isolated from tryptic digests of human EI and are given as Sequence I.D. Numbers 1-11. The sequences of each of these eleven peptides are contained within the deduced sequence of the human EI gene (see Table 1, and Sequence I.D. Number 12).

TABLE 1

| Tryptic Peptides of Human Elastase Inhibitor | |
|---|---|
| Sequence I.D. Number | Amino Acid Position in Deduced Sequence[a] |
| 1 | 178-186 |
| 2 | 130-137 |
| 3 | 58-68 |
| 4 | 112-128 |
| 5 | 291-299 |
| 6 | 261-274 |
| 7 | 98-110 |
| 8 | 216-237 |
| 9 | 245-254 |
| 10 | 276-289 |

TABLE 1-continued

| Tryptic Peptides of Human Elastase Inhibitor | |
|---|---|
| Sequence I.D. Number | Amino Acid Position in Deduced Sequence[a] |
| 11 | 204-213 |

[a]See sequence I.D. No. 12

Existence of Disulfide Bonds.

200 mM of mercaptoethanol does not adversely affect the ability of pure Human EI to form a complex with elastase. EI therefore does not appear to contain disulfide bonds, and in particular does not contain disulfide bonds that are essential for activity.

Essential Cysteine Residue.

Addition of the sulfhydryl iodoacetamide (3 mM) to pure Human EI causes almost complete loss of covalent complex activity with elastase. Destruction of unreacted iodoacetamide by addition of mercaptoethanol or removal by dialysis does not restore activity to pure Human EI. EI therefore appears to have a cysteine residue that is essential for the formation of the covalent elastase-EI complex.

Demonstration of EI in Monocytes, Macrophages and Neutrophilis.

Figure 5:
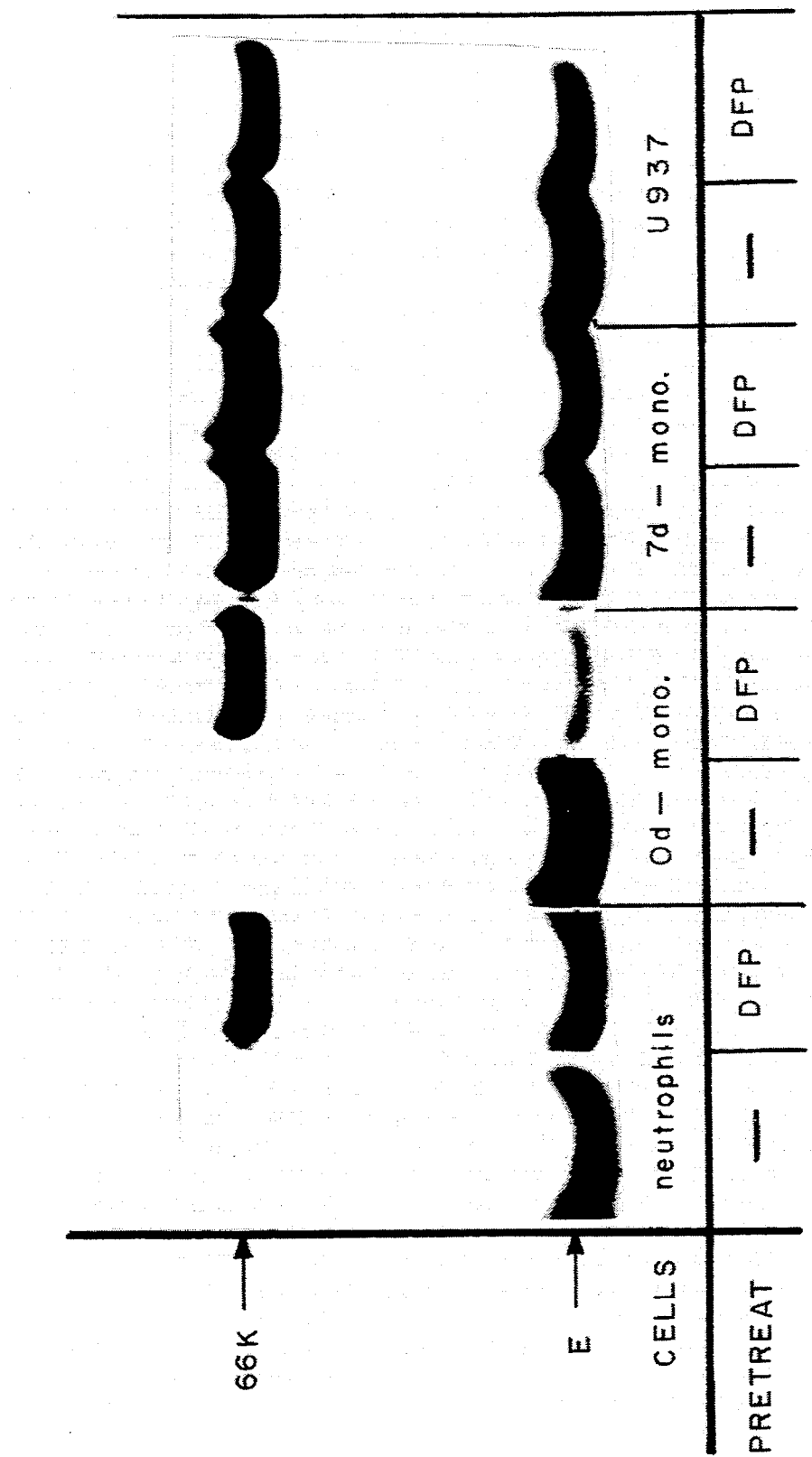
FIG. 5 is an autoradiograph showing the presence of Human EI in monocytes, neutrophils and U937 cells.

Human EI was detected using the $^{125}I$-elastase complex assay in lysates of human monocytes matured in culture and in the monocyte-like ceil line U937-EI, but was not detected in freshly isolated human monocytes or neutrophils. When these latter cells were incubated with the active site reagent diisopropyl fluorophosphate (DFP) and lysed in the presence of DFP, and excess DFP removed from lysates by dialysis, Human EI activity was readily detected in fresh monocytes as well neutrophils (FIG. 5). Human EI activity was also detected in lysates of pulmonary macrophages obtained by broncholavage of healthy nonsmoker volunteers.

Cloning Hyuman EI.

(1). RNA Isolation and Analysis.

The isolation of RNA was critical to the isolation of the cDNA clone for human elastase inhibitor. Total mRNA was isolated from U937-EI cells and "back translated" to cDNA using conventional procedures. Specifically, total RNA from both U937-EI cells and CEM human lymphoblastoid cells was isolated from guanidinium thiocyanate and mercaptoethanol-lysed cells by cesium chloride centrifugation (Chirgwin et al., *Biochemistry*, 1979, 18:5294-5299). Poly(A)+ RNA was isolated by oligo(dT) chromatography (Aviv and Leder, PNAS, 1972, 69:1408-1412). RNA analysis was performed to confirm the presence of the mRNA for human elastase inhibitor in the monocyte-like cell line U937 and its absence in the lymphoblastoid cell line CEM. Accordingly, RNA for Northern analysis was size-fractionated by formaldehyde/agarose electrophoresis (Maniatis et al., *Molecular Cloning*. Cold Spring Harbor Laboratory, 1982) with RNA sizing markers (Gibco, BRL, Grand Island N.Y. 14072) in a parallel lane, and transferred to nitrocellulose. An insert of cDNA clone UC-10 (described below) labeled with $^{32}P$-dCTP by random prime labeling (K. Moreman, *PNAS*, 1989, 86:5276-5280; Royer-Pokora et al., Nature, 1986, 332:32-38) served as the probe. Northern analysis (not shown) revealed hybridization with the probe for RNA isolated from the monocyte-like cell line U937 but no detectable hybridization for mRNA in the lymphoblastoid cell line CEM. The U937 cell mRNA species had sizes of 2.6 kb, 1.9 kb and 1.5 kb. The 1.5 kb fragment had a size corresponding approximately to the size of the composite cDNA sequence of HL-Al or U′Al amplified products and sequence I.D. number 12. These clones are described below and in FIG. 6.

(2) Preparation and Analysis of DNA.

Synthesis of a cDNA for the human elastase inhibitor gene is essential for the cloning of the gene. Accordingly, cDNA corresponding to poly(A)+ RNA isolated from U937-EI cells was synthesized as described by Moreman, PNAS, 1989, supra). Moreman provides a detailed procedure for the mixed oligonucleotide primed amplification of cDNA ("MOPAC"). The MOPAC method is divided into three principle steps: (1) cDNA synthesis, (2) designing of oligonucleotide primers, and (3) amplification of cDNA using the polymerase chain reaction ("PCR").

Synthesis of the cDNA for the human elastase inhibitor using the MOPAC procedure was performed using a reaction volume of 100 ul containing 200 units of murine leukemia virus reverse transcriptase (Gibco, BRL), enzyme buffer (Gibco, BRL), 5 ug of U937 cell poly(A)+ RNA, 40 units of RNasin (Promega), 1 mM of each dNTP, and 15 ug/ml random hexanucleotide primers (Promega) at 37° C. for 1.5 hours. The mixture was extracted with phenol/chloroform/isoamyl alcohol (25:24:1) and desalted on a Sephadex G-50 column (Pharmacia, Piscataway, N.J. 08855) equilibrated in 10 mM Tris-HCl buffer, pH 8.0 containing 100 mM KCl. Following extraction, the mixture was designated the cDNA synthesis product and amplified as described below.

(3) Mixed Oligonucleotide Primed Amplification of cDNA ("MOPAC").

MOPAC amplification requires two or more oligonucleotide primers encoding non-contiguous peptide sequences with known relative locations. In order to identify the relative locations of peptide sequence I.D. Numbers 1 through 11, a computer program was initially used to identify regions of sequence homology between the monocyte peptides and known Serpin proteins. Analysis of the monocyte peptides was important for performance of the MOPAC procedure.

The program LFASTA (provided by Dr. William Pearson, CharlotTesville, Va.) was used to detect regions of partial sequence homology between peptide sequence I.D. Numbers 1 through 11 and known Serpin proteins according to the method of Pearson and Lipman (PNAS, 1989, 85:5276–5280). The programs allowed peptide Sequence I.D. Numbers 1 through 11 to be tentatively located relative to each other by first identifying the relative positions of corresponding peptides in known Serpin proteins. The LFASTA program results indicated the following relative positions of the human elastase inhibitor peptides: peptide I.D. Number 3 at residues 79–95, peptide I.D. Number 4 at residues 137–154, peptide I.D. Number 8 at residues 239–255, and peptide sequence I.D. Numbers 5 and 10, contiguous between residues 291–314. Standard Serpin numbering was used (Carrell et. al., Protease Inhibitors pp.403–420; A. Barrett and G. Salvesan, eds, Elsevier, Amsterdam 1986).

Oligonucleotide sense primers were designated corresponding to peptide I.D. Numbers 3 and 4, and antisense primers were designated corresponding to peptide I.D. Number 8 and contiguous I.D. Numbers 5 and 10. Primers were synthesized by the phosphoramidite method on an Applied Biosystems Model 380B synthesizer (Foster City, Calif. 94404). Codon degeneracy was taken into account in the design of oligonucleotide primers by using the most frequently occurring codon for a particular amino acid, using mixtures of nucleotide triphosphates, or by deoxyinosine substitution as described by Moreman (PNAS, 1989, 86:5276–5280).

Amplification of U937 cell cDNA was performed using pairs of the above-described primers. The cDNA synthesis product from poly(A)+ RNA (5 ul) was amplified according to standard procedures (K. Moreman, PNAS, 1989, 86:5276–5280) in 100 ul containing 10 mM Tris-HCl buffer, pH 8.3, 50 mM KCl, 1.5 mM MgCl$_2$, 0.01% gelatin, 200 uM of each dNTP, and 0.5 uM of the above-disclosed primers. Following the addition of 2.5 units of Thermus aquaticus (Taq) polymerase (Perkin-Elmer/Cetus Inc., Norwalk, CT 06859) with 100 ul of mineral oil overlay, the amplification mixture was incubated in a DNA Thermal Cycler (Perkin-Elmer Cetus, Inc. for 30 cycles, each cycle comprising incubation for 1 min. at 92° C., for 2 min. at 50° C., and for 3 min. at 72° C.

The MOPAC-amplified cDNAs were resolved by electrophoresis on 1% low melt agarose containing ethidium bromide at a concentration between 0.5 and 1 ug/ml. Electrophoresis revealed that amplification of U937 cell cDNA with pairs of the above-disclosed MOPAC primers resulted in single dominant products which were readily detected by ethidium bromide staining (not shown). The amplified cDNA fragments had sizes consistent with the LFASTA peptide localization, i.e., one product contained 510 bp (the product of primers corresponding to peptides I.D. Numbers 3 and 8); another product contained 340 bp (the product of primers corresponding to peptides I.D. Numbers 4 and 8); one product contained 720 bp (corresponding to combined peptide I.D. Numbers 3 and combined peptides 10 and 5); and one product contained 550 bp (the product of primers corresponding to peptide I.D. Numbers 4 and combined peptides 10 and 5).

(4). Preparation of Probes for Screenign cDNA Libraries.

The amplified cDNA fragment containing 550 bp, described above, was subsequently labeled with $^{32}$P-dCTP by random priming (Feinberg and Vogelstein, Anal. Biochem, 1983, 132: 6–13). This probe was used to screen 700,000 clones of a U937 cDNA library. The screening procedure is described below.

(5). Description of cDNA Libraries.

In general, a cDNA library is prepared by inserting each cDNA molecule into a vector, such as for example into the phage λgt11 or λ-ZAP II (Uni-ZAP, Stratagene, La Jolla, CA 92037). Alternatively, a human monocyte or monocyte-like cDNA library in a vector such as λt11 may be purchased. The vectors are not limited to those capable of replication in bacterial systems but also include vectors capable of replication in mammalian or other types cf cell lines.

A cDNA library in a bacterial vector is generally expressed in E. coli and grown up to ~105 E. coli colonies, each plaque derived from one infected bacterium. The colonies then are screened to identify those colonies containing the λgt11 phage including the monocyte cDNA of interest. The detection probe for screening the E. coli colonies may be either an oligonucleotide encoding a portion of Human EI, or an antibody or antibodies to Human EI. The appropriate oligonucleotide probes disclosed herein are based upon the human EI sequencing data presented above. The probes have been prepared according to the MOPAC method, an improved variation of conventional techniques. The MOPAC method could be utilized because of the availability of (1) sequence of tryptic peptides of pure human EI, (2) a program for comparing protein sequence homology and (3) our knowledge that human elastase inhibitor is a member of the Setpin family of proteins.

Alternatively, appropriate screening antibodies are prepared by conventional immunization techniques using purified Human EI as the immunogen. Peptides are alternatively synthesized by conventional procedures using sequences of EI peptides and used as immunogens to generate anti-Human EI antibodies. When the colony of interest is identified, the cDNA from the expression vector in that colony is isolated and the genomic complement to the cDNA for Human EI is isolated, all according to conventional techniques.

In the embodiment described herein, three independent cDNA libraries were used to identify the gene for human elastase inhibitor.

(a) λ-ZAP II Library:

Preparation of this library was performed by Stratagene (La Jolla, Calif.) using the U937 cell cDNA described above (corresponding to poly(A) selected RNA) by unidirectional insertion into a λ-ZAP II vector (Uni-ZAP, Stratagene). The λ-ZAP II Library is now commercially available from Stratagene. The amplified cDNA product (generated by primers corresponding to peptide numbers 3 and combined peptide numbers 5 and 10 and containing 550 bp) was used as a probe to screen 700,000 clones of the λ-ZAP II Library. A total of fifteen positive clones by duplicate screening were selected for further analysis. Positive colonies were plaque purified according to standard procedures (see e.g., Maniatis, et al. supra).

Phage λ-ZAP II contains the plasmid pBluescript SK into which the mammalian cDNA is inserted. The use of the phage is advantageous in that the pBluescript plasmids can be used directly for DNA sequencing. Accordingly, the pBluescript plasmids containing all or part of the putative elastase inhibitor cDNA were obtained by in vivo excision as described by Strategene in the product literature which accompanied the λ-ZAP II (Uni-ZAP) vector.

The cloned DNA inserts were subjected to electrophoresis on low melt agarose gels. Of the selected clones, three clones having inserts greater than approximately 0.8 kb were partially or completely sequenced. The cDNA inserts contained in these clones were designated U-1 (complete sequence); U-5 (partial sequence), and U-10 (complete sequence). (See FIG. 6) However, none of the clones, alone or together, yielded the sequence of a complete open reading frame for the elastase inhibitor gene. Accordingly, the DNA segment corresponding to the missing 5' region of the elastase inhibitor gene was isolated from two additional independent cDNA libraries: the λ-gt11 and λ-gt10 libraries.

(b) λ-gt11 Library:

A U937 cell cDNA library in λ-gt11 was purchased from Clontech Laboratories, Palo Alto, Calif. 94303.

(c) λ-gt10 Library:

A λ-gt10 library from HL60 promyelocytic cells (Collins et al., PNAS, 1978, 75:2458) induced toward granulocytic differentiation (Newburger et al., *J. Biol. Chem.*, 1984, 259:3771) by dimethylformamide treatment (Royer-Pokora et al., *Nature*, 1986, 332:32–38; Parkos et al., PNAS, 1988, 85:3319) was provided by Dr. Stuart Orkin, Children's Hospital, Boston, Mass.

(6). Generation of the 5'Region of the human elastase Inhibitor gene by Amplification of Library cDNAs.

To complete, the sequence for the elastase inhibitor cDNA, segments corresponding to the missing 5'-region were amplified using total DNA from two independent cDNA libraries as template, a flanking vector sequence as the sense primer, and clone U-10 as the antisense primer.

Specifically, λ-gt11 and λ-gt10 libraries were separately used as sources of DNA for direct amplification using a modified standard polymerase chain reaction (PCR) amplification procedure as described by Rosenberg et al. (*Biotechniques* 1991, 10:53–54). The DNA was pelleted by centrifugation. An amount of DNA corresponding to $10^5$–$10^7$ plaque forming units (pfu) was denatured and was incubated in a 100 ul of a standard reaction mixture (Rosenberg et al., supra).

The antisense primer was an 18-mer (18 nucleotides) corresponding to clone U-10 residues 590–607. For DNA isolated from the λ-gt11 library, the sense primer was a 24-mer (product #1218, New England Biolabs, Beverly, MA) corresponding to the λ-gt11 vector flanking sequence in the forward direction. For DNA isolated from the λ-gt10 library, the sense primer (product #1231, New England Biolabs) was a 21-mer corresponding to the λ-gt10 vector flanking sequence in the forward direction.

The amplification reaction mixture was overlayed with 100 ul mineral oil and allowed to proceed for 40 cycles, each cycle comprising 1 min. at 92° C., 2 min. at 55° C., and 3 min. at 72° C. Following gel electrophoresis, amplification products having approximately 800 bp were excised from the gel and used as a template for a second amplification reaction, using the buffers and reaction conditions described above. The predominant product of the second amplification reaction, which was approximately 800 bp, was gel-purified and used as a template in a third amplification reaction.

The third amplification differed from the prior amplification reactions in that (1) the third amplification consisted of 6–8 parallel 100 ul reactions and (2) substituted an 18-mer antisense primer corresponding to UC-10 residues 182–199 for the antisense primer used originally in the first and second amplification reactions.

An amplified product (U'-Al) containing approximately 460 bp was generated using DNA isolated from the λ-gt11 library. Similarly, an amplified product (HL-Al) containing approximately 460 bp was generated using DNA isolated from the λ-gt10 library. (See FIG. 6) These products were purified by gel electrophoresis, extracted with phenol/chloroforms, and ethanol precipitated in preparation for DNA sequencing. The inserts of the isolated clones in the plasmid pBluescript and the double stranded amplified DNA products were sequenced by the dideoxy chain termination/extension reaction (Sanger, PNAS, 1977, 74:5463–5467) using Sequenase reagents (U.S. Biochemicals), and vector-specific primers and 18-mer primers based on the elastase inhibitor sequence as it became known.

(7). Nucleotide Sequence of Human Elastase Inhibitor.

Figure 6:
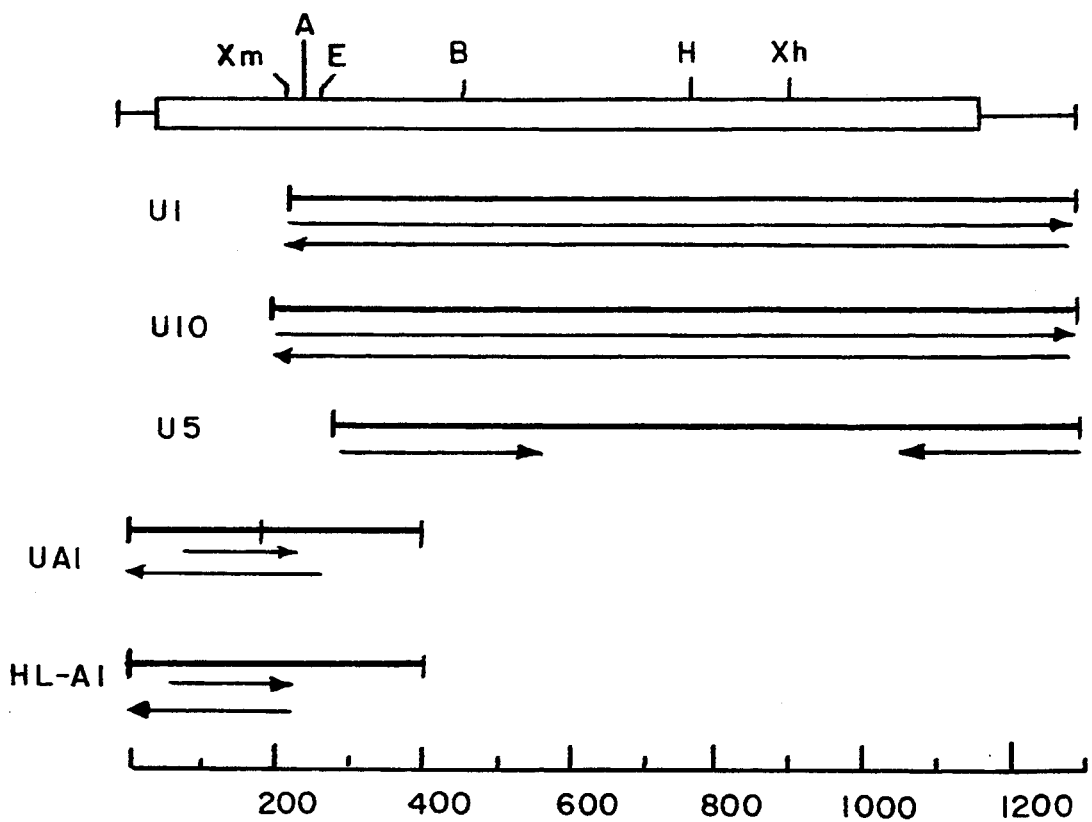
FIG. 6 is a schematic diagram of the restriction map of human EI cDNA.

The inserts of the clones and extension products were sequenced by the strategy outlined in FIG. 6. The open box in the upper part of FIG. 6 represents the protein coding region. The scale at the bottom indicates the nucleotide positions. Not all overlapping segments were sequenced. However, all overlapping segments which were sequenced were identical, except at base 1289 t be explained later in this section. The lengths of clones U-10, U-1 and U-5 and amplification products U'-Al and HL-Al, are indicated (FIG. 6). The regions which were a sequenced by solid overlapping reactions, are indicated by lines with directional arrows (FIG. 6). The composite sequence (sequence I.D. Number 12) was 1316 nucleotides long and includes a single open reading frame and a poly(A) tail containing at least 18 residues. The open reading frame begins at position 49 with the first methionine codon, part of the sequence AC-CATGG, the proposed optimal sequence for initiation by eukaryotic ribosomes (Kozak, Cell, 1986, 44:283). The reading frame terminates with a stop codon at position 1186. The open reading frame is followed by a 3' untranslated region of 109–113 nucleotides including a single polyadenylation signal, AATAAA, beginning at residue 1277, and the poly(A) tail. The only sequence difference observed between the clones is present at residue 1298. This residue is C in clones U-1 and U-5 and is A in clone U-10 (FIG. 6). ( (8). Derived Amino Acid Sequence.

The open reading frame encodes a polypeptide of 379 amino acids with having a molecular weight of 42,686 and the composition of $Asn_{23}$ $Asp_{18}$ $Gln_{11}$ $Glu_{30}$ $His_7$ $Lys_{29}$ $Arg_{13}$ $Ala_{30}$ $Cys_2$ $Gly_{20}$ $Tyr_{10}$ $Val_{18}$ $Ile_{19}$ $Leu_{41}$ $Phe_{27}$ $Met_{12}$ $Trp_3$ $Pro_{12}$ $Ser_{31}$ $Thr_{23}$. The amino acid sequence of the open reading frame for the human elastase inhibitor is shown in sequence ID number 12. The deduced sequence includes all of the tryptic peptides shown in Table 1. The encoded polypeptide sequence is unique. A search of the complete data base at the National Biomedical Research Foundation, Washington, D.C.(September, 1991) using the FASTA program (Pearson and Lipman, PNAS. 1988, 85: 2442–2448) did not reveal any proteins having identical or nearly identical sequence homology.

Several features of the derived polypeptide sequence confirm the composite cDNA as encoding human EI. The length of the derived polypeptide sequence, 379 is quite close to the length of approximately 360 amino acids determined by measuring the electrophoretic mobility of pure human EI. Significantly, the derived molecular weight of 42,686 is quite close to the approximate molecular weight of about 42,000 determined on the purified protein. The derived amino acid composition is similar, although not identical, to the amino acid composition determined for purified human EI (FIG. 4).

More importantly, the sequences of the eleven tryptic peptide prepared from isolated human EI (sequence I.D. Numbers 1 through 11) are contained within the 379 residue deduced sequence. Functional data obtained with human EI had indicated that human EI is a member of the Serpin family of proteins with related sequence. and structure. As presented below, the derived sequence encodes a member of the Serpin protein family. Comparison of the derived polypeptide sequence with databank sequences as described above revealed strong partial identity with several previously described proteins, all of which are members of the Serpin family. For polypeptides of this length, identity greater than 25% indicates that the two molecules are very likely genuinely related (R. F. Doolittle, *Of URFS and ORFS, A Primer on How to Analyze Derived Amino Acid Sequences*, University Science Books, Mill Valley, Calif., 1986). The four most closely related Serpin sequences are: gene Y (42.7% identity); plasminogen activator-2 (40.4% identity); ovalbumin (39.8% identity); and antithrombin III (39.3% identity). Moreover, the treatment of pure human EI with iodoacetamide abrogated its ability to form a complex with elastase and indicated that human EI has an essential cysteine residue. Use of the program FASTA to align the derived sequence with data bank Serpin sequences indicate that the active site residue in the derived sequence is cysteine at position 344.

(9). Southern Analysis.

Total genomic DNA from U937-EI cells was isolated, digested with the restriction enzymes EcoRI and Hind III and subjected to Southern analysis using a probe prepared from the U-10 insert as described above. Southern analysis (not shown) identified single hybridizing bands of 4.5 and 6.5 bp, suggesting that the human elastase inhibitor is encoded in humants by a single copy gene.

(10) Restriciton Enzyme Anaylsis

Computer analysis of the composite cDNA sequence identified unique sites for cleavage by restriction enzymes, some of which are as follows: XmnI at residue 242, AlwNI at residue 264, EcoRV at residue 276, BspEI at residue 480, HincII at residue 795, XhoII at residue 930 (FIG. 6).

The first three sites are located in the overlap region; residues 216–414 are present in the DNA extension products and in isolated clones U-1 and U-10. Either the enzyme AlwN, EcoRV or XmnI, all of which are available commercially, for example from New England Biolabs (Beverly, MA) can be used to generate a composite clone by restriction cleavage, and isolation and ligation of the DNA fragments.

(11). Preparation of Recombinant Human EI.

The absence of significant carbohydrate levels in protein preparations as well as the insensitivity of the molecule oo the glycosidase PNGase F indicates that human EI is a non-glycosylated protein. Moreover, as discussed below, human EI is free of disulfide bonds.

The presence of at least one free sulfhydryl cysteine residue in human EI is indicated by two lines of evidence; adherence of the molecule to a mixed disulfide affinity resin and inhibition of its elastase inhibitory activity by the reagent iodoacetamide. Since the derived sequence contains only two cysteine residues (Cys-214 and Cys-344: Sequence I.D. Number. 12), it follows that both cysteine residues have free sulfhydryl groups and that the molecule lacks disulfide bonds. Preparation of recombinant human EI will be simplified by the absence of glycosylation and the absence of disulfide bonds since all expression systems are expected to be suitable for generating recombinant human EI. These include expression in E. coli, yeast, Baculovirus and COS cells.

To prepare recombinant human EI, a full length clone corresponding to Sequence I.D. Number 12 is first prepared from the clone U-10 and the amplified product U'-Al. Each of these is cleaved by a restriction endonuclease, which cleaves only at a single site located within the region common to the clone and the amplified product, namely residues 216 to 414. As shown in FIG. 6, the restriction enzymes AlwNI, EcoRV and XmnI, cleave at single sites located within this region at residues 242, 264, or 276, respectively, and can be used to generate a composite full-length clone. For example, the pBluescript plasmid containing the U-10 insert (pBSK-U10) is digested to completion with EcoRI restriction endonuclease and then subjected to partial digestion with AlwNI restriction endonuclease. Partial digestion is necessary because pBSK-U10 contains two AlwNI sites, one at the upstream end of the insert and one at position 1559 in the vector. Single cleavage at the upstream end of the insert gives an approximately 4,000 bp product. Single cleavage at vector residue position 1559 as well as double cleavage gives two products, about 3200 bp and about 800 bp. The 4,000 bp partial digestion product is readily separated from the other products, which are approximately 2000 bp in length, by electrophoresis on 1% agarose (Maniatis et al., Supra). The U'-Al amplified product (upstream fragment) is amplified by the polymerase chain reaction using upstream and downstream primers. The upstream primer overlaps the upstream 15 nucleotides of U'-Al plus an additional 10 nucleotides containing the EcoRI recognition site GAATTC. The downstream primer consists of 25 nucleotides centering on the AlwNI site in the U'-Al sequence.

Following PCR amplification, this amplified material is subjected to digestion with EcoRI and AlwNI, purified by gel electrophoresis, mixed with the vector-U10 material prepared above, ligated, and transformed into E. coli, for example the E. coli strain HB101. The resulting clones are verified either by restriction mapping analysis or by direct sequencing. Alternatively, a semi-synthetic approach employing synthetic oligonucleotideis used to prepare a U'-Al fragment to be joined to the above-described vector-U10 material.

Alternatively, a full-length clone is isolated from an appropriate monocyte-like cDNA library, such as the Clontech library described herein, in which case amplified product U'-Al or HL-Al is used as hybridizing probe in the screening step.

It will be understood by those skilled in the art that there may be multiply related, but slightly different forms of naturally-occurring Human EI. Therefore, it further will be understood that there may be more than one mRNA sequence and more than one corresponding cDNA sequence encoding for naturally-occurring Human EI. However, each such DNA sequence may be isolated according to the procedures set forth above and each form of Human EI may be obtained by expression vectors carrying each such cDNA sequence. Likewise, the genomic DNA corresponding to the various forms of Human EI then may be isolated in a conventional manner.

It will be understood by those skilled in the art that there are many other equivalents to the foregoing description of the preferred embodiment. While the invention provides, among other things, a method for obtaining a cDNA copy of the mRNA for Human EI and the expression of that cDNA, various functional variations of the cDNA and the expressed product are contemplated as within the scope of the invention.

For example, cDNA sequences encoding Human EI may be changed at one or more base-pair positions or portions of the cDNA may be deleted while still retaining the ability of the expressed protein to act as an inhibitor of elastase or of other serine proteinases. The expressed protein therefore may include amino acid substitutions or deletions yet still be the functional equivalent of naturally occurring Human EI.

As an example, the degeneracy of the genetic code results in many amino acids being specified by more than one codon. Accordingly, a genetically engineered cDNA for Human EI, includes a DNA sequence corresponding to the naturally occurring gene, a sequence corresponding to a non-naturally occurring gene having nucleotide substitutions which do not affect the amino acid sequence of the translation product of the gene, and sequences corresponding tc variations, derivatives or portions thereof that maintain the ability of the cDNA to be translated into a protein product having the ability to complex with and/or inhibit the activity of elastase. Thus, genetically engineered Human EI, includes naturally and non-naturally occurring Human EI, and variations, derivatives or portions thereof that maintain their ability to complex with and/or inhibit the activity of elastase.

As another example, the polymerase chain reaction (PCR) technique produces DNA sequence changes by manipulating oligonucleotide primers rather than by manipulating DNA fragments with restriction and ligation enzymes. PCR products readily accept such sequence changes as 5' "add-on" sequences to the primers. Furthermore, the efficiency at which the modified product is produced is nearly 100%. A restriction site sequence is easily introduced into a DNA fragment produced by PCR merely by attaching these sequences to the 5' ends of the oligonucleotide primer. (Scharf et al., 986, Science 223:1076). Although these sequences are mismatched to the template DNA, in most cases they have little effect on the specificity or efficiency of the amplification because specificity is primarily imparted by the 3' end of the primer. As strands initiated by these "add-on" primers are themselves copierS, the added restriction site sequence becomes fixed into the growing population of PCR product fragments. The principle of introducing DNA alterations by way of PCR primers can be used to help create DNA fragments altered in sequence at any position in, or to recombine DNA sequences at any desired junction.

Using PCR methodology, a generalized mutagenesis protocol is accomplished by developing oligonucleotide primers that are mismatched to the target sequence at at least a single base. This primer-introduced sequence modification is limited by length constraints on the chemical synthesis of the primer. Nevertheless, this process is used with PCR to combine PCR products from different sections of the sample DNA template such that the resulting fragments overlap in sequence. The overlapping PCR products, containing the site-directed mutation, are mixed, denatured and allowed to reanneal. This process of PCR fragment joining is a means of introducing a sequence alteration at any position in the fragment, nct just at the end. (See generally, Mullis, K, et al, 1986, Cold Spring Harbor Symposium 51:263). A specific protocol for site-directed mutagenesis and recombination using PCR can be found in Higuchi, "Using PCR to Engineer DNA", pages 68–69, in *PCR Technology* ed. H. Erlich, Stockton Press (1989). Since the overlap necessary to effect the combination need not exist in the natural DNA template, but can be made as an add-on sequence to the primers, PCR is used to create specific site substitutions, deletions, and insertions at nearly any position in a DNA fragment as well as to combine previously unrelated sequences at precise junctions. These techniques have previously been used to place substitutions in the middle of a 300–800 bp PCR fragment, Higuchi, R. et al, 1988, *Nucl. Acids Res.* 16:7351. Insertions and deletions as add-on sequences have been demonstrated by Vallette et al., 1989, *Nucl. Acids Res.* 17:723, and the precise recombining of four different sequences to cremate a 970-bp DNA fragment coding for a chimeric protein has been shown by Horton et al., 1989, Gene 77:61.

The PCR method is an easy way of creating specific new DNA sequence combinations and can be used in conjunction with tests to determine the presence or absence of elastase inhibitor activity (7,8) to provide a method for creating a functional variant of the human elastase inhibitor protein.

Such a method includes the steps of cloning a human elastase inhibitor cDNA using the methods outlined herein; introducing restriction site sequences, insertions, deletions or other site-directed modifications into this DNA sequence using, for instance PCR methods; inserting the resulting DNA product into an appropriate expression vector using the known restriction sites as discussed herein or, ultimately introducing known restriction sites into the DNA sequence with PCR methodology; expressing the modified DNA in an appropriate expression system, for which a wide variety of vectors is available; expressing the resulting human elastase inhibitor product and testing the ability of this product to form a covalent complex with elastase (7,8). Subsequently, the expression product is purified for diagnostic, therapeutic or other applications.

Functional variations of human EI with altered active site sequences, particularly, but not limited to, the P1 residue adjacent to the cleavage bond, can be prepared to have altered inhibitory activity toward elastase and other serine proteases. The correlation of the spectrum of inhibited protease with the nature of the P1 residue was demonstrated for the case of $\alpha$1-antitrypsin by the study of recombinant variant molecules prepared by site-directed mutagenesis of the reactive site P1 residue (See, for example Matheson, N. R. et al., 1986, *J. Biol. Chem.*, 261: 10404–10409; Courthey, M. et al., 1985, *Nature* 313: 149–151). This approach, which has found applicability also for other Serpin molecules including antithrombin III (1), demonstrates that active site mutants of Serpin molecules, particularly P1 variants, can be generated which have increased or decreased inhibitory activity (measured as second order association rate constants) for particular serine proteases.

In a similar manner, active site variants can be produced with altered stability to oxidants, a feature that might be important in the case of human EI, which like $\alpha$1-antitrypsin, has an oxidation sensitive residue in the active site. Variants of human EI can be produced by techniques including site-directed mutagenesis in which the active site P1 Cys residue is replaced by an oxidation resistant residue such as Val or Ala (which resemble Cys in size, hydrophobicity and lack of charge) in order to generate a variant EI molecule with similar inhibitory properties but that is resistant to inactivation by oxidants such as those produced by cigarette smoke and by active phagocytic cells. Generation by site-directed mutagenesis of recombinant $\alpha$1-antitrypsin variant molecules in which the oxidation sensitive Met residue was replaced by either Val or Ala did not greatly alter the elastase inhibitory activity but the mutant molecules were resistant to denaturation by oxidants (Matheson et al., supra).

Variant human EI with increased resistance to oxidants may be preferred for some applications, since the amount needed for a pharmacologically desirable inhibitory function would be reduced. However, in most cases, human EI and EI variants that are oxidation sensitive may be preferred. Both Serpin superfamily molecules, *alpha1*-antitrypsin and EI, which function as effective elastase inhibitors, have P1 residues, which are oxidation-sensitive. This coincidence is not explained by particularly close relatedness of the molecules, because, they have (only) 30.3% identical residues compared for example to 42.7% identical residues in human EI and plasminogen activator inhibitor II. Moreover, the oxidation sensitive P1 residue is not the same in the two inhibiters. Thus, oxidation sensitivity seems to have evolved independently in two of two Serpin elastase inhibitory molecules, perhaps reflecting the need for elastase inhibitory molecules to act at specific locations and for restricted times.

By site directed mutagenesis or more recently developed methods such as PCR-based methods, described above, recombinant variants, derivatives or portions of EI can be produced with one or more altered residues particularly P1 and other active region residues, so as to completely alter the inhibitory properties of human EI and render the variant molecule useful in other applications. A mutant human EI recombinant molecule with Arg substituted in P1 position with or without additional substitutions can have greatly reduced elastase inhibitory activity and can function instead as an inhibitor of thrombin, as for example, an anti-clotting agent. Alternatively, recombinant human EI variants with P1 Arg can function to inhibit plasminogen activator of C1-esterase and function in different applications. Other variants and applications are also envisioned within the scope of the present invention.

In this regard it will be understood by those skilled in the art that a molecule may inhibit the activity of elastase without forming a covalent complex with elastase. Thus portions of Human EI, and preferably those having the sequence of the elastase binding region cf Human EI can have sufficient affinity for elastase so as to bind to and inhibit elastase, but nct form a covalent complex with elastase. Such portions or derivatives thereof are contemplated as within the scope of the invention. These portions or derivatives may be prepared by conventional peptide synthesis or recombinant techniques.

The invention also contemplates portions and variations of Human EI coupled with moieties capable of reacting with the active site of a serine proteinase. In this instance, the portion or variation recognizes the serine proteinase and delivers the active moiety for inhibitory interaction with the serine active site.

Human EI also can be useful in inhibiting other serine proteases in addition to elastase. For Serpin molecules, the spectrum of inhibited proteases is determined in a general way by the residues in the active site, particularly the PI residue adjacent to the cleavage bond. Thus, a naturally occurring mutant of $\alpha$1-antitrypsin in which the P1 residue had mutated from Met to Arg, functioned poorly as an inhibitor of elastase and was a very effective inhibitor of thrombin, which is not normally inhibited by $\alpha$1-antitrypsin (Owen, M.C. et al., N. Engl. *J. Med.* 694–698). Although some Serpin molecules have sharply defined specificities, inhibiting primarily a single serine protease, others including $\alpha$1-antitrypsin which has a Met residue in the P1 position, have somewhat broader specificity. The counterpart molecule of human EI in guinea pigs inhibits both elastase and trypsin (E. Remold-O'Donnell and Lewandrowski, 1983, *J. Biol. Chem.*, 258:3251). Moreover, a recombinant mutant of $\alpha$1-antitrypsin with a Cys residue in the P1 site, as is found in the derived Human EI sequence, inhibited both elastase and chymotrypsin (Matheson et al., supra). Thus, functional studies can be carried out using recombinant human EI to reveal that human EI inhibits more than the one serine protease. In particular, human EI may function to inhibit proteinase 3 (Kao, R.C. et al., 1988, *J. Clin. Invest.* 82:1963–1973) and/or cathepsin G (Salvesan, G. et al., 1987, *Biochemistry* 26:2289–2293). Both of these proteinases are serine proteases found with elastase in the azurophil granules of neutrophils and also contribute to degradation of extracellular matrix proteins in disease states. Likewise, human EI may function naturally or may have pharmacological application in the inhibition of the serine proteases (e.g. Hayes, M.P. et al., 1989, *J. Exp. Med.* 170:933–946) in granules of cytolytic T lymphocytes, natural killer cells and mast cells and may have application in preventing adverse action of these proteases.

Portions of Human EI also may be used as inhibitors of Human EI. For example, portions of Human EI that interact with elastase but that do not interfere with the activity of elastase, may be used to block in vivo the inhibitory action of Human EI by preventing the Human EI-elastase complex from forming. Thus, it will be understood by those skilled in the art that the products of the invention include portions of Human EI not capable of forming a covalent complex with elastase and oligonucleotides encoding such portions.

The naturally occurring Human EI and variations, derivatives and portions thereof may be used in pharmaceutically effective amounts to treat medical conditions. Generally, they may be used for treatment of conditions involving destructive action by elastase and by other proteinases with which they react, including tissue destruction as a consequence of inflammation. Specific applications include bronchiectasis as a consequence of inflammation in the lung, intestinal tissue damage in chronic granulatomous disease and LAD (leukocyte adhesion deficiency), cystic fibrosis, pancreatitis, malignancies, blood damage vessel due to clotting, blistering skin disorders, reperfusion injury, and ulcerative coliris. Other applications include all conditions where Human EI level is abnormal, elastase or other proteinases reactive with Human EI or variants of human EI are in excess, or when there is phagocyte accumulation in excess.

The naturally-occurring Human EI and variations, derivatives and portions thereof also may be employed to create antisera for the detection of the presence or absence or the quantity of Human EI, useful in evaluating congenital or acquired deficiencies and also in evaluating disease states. For example, antibodies to Human EI may be used to evaluate the level of phagocylic cell response in infectious disease states such as tuberculosis and leprosy. Likewise, such antibodies may be used to diagnose inflammatory states such as rheumatological diseases (e. g., rheumatoid arthritis), immunological diseases (e.g., pemphigus), idiopathic diseases (e.g., sarcoidosis) and inflammatory diseases (e.g., adult respiratory distress syndrome.) Antibodies further may be used as a diagnostic tool in connection with neoplastic disearses (e.g., monitoring of malignancies by evaluation of host response, evaluating the metastatic capacity of malignant cells), in genetic diseases (e.g., cystic fibrosis or hereditary abnormalities in the elastase-elastase inhibitor system), in abnormal maturation of myelomonocytic cells (e.g., Chediak-Higashi syndrome), in pancreatitis and other disorders of the pancreas, and generally for evaluation of the genetic variability of the human EI-proteinase system in the population and its relationship to diseases.

Antibodies to Human EI also have therapeutic uses, including treatment of conditions in which elastase functions abnormally, elastase inhibitor is in excess over elastase, or phagocyte recruitment is defective. Such conditions include abnormality and susceptibility to infections or inadequate immune defense. For the case of human EI or human EI variants which are oxidation sensitive, agents can be added, including but not limited to glutathione and N-acetyl cysteine, which would decrease the rate of oxidation inactivation. Such agents could be mixed with human EI or EI variant or can be chemically incorporated in the form of a modified human EI molecule.

In order to target recombinant EI or EI variants to particular physiological sites, altered sequences can be introduced at one or more sites in the overall sequence, for example by PC based methodology. Alternatively, targeting moieties can be chemically incorporated into human EI or EI variants. Mareover, targetting of recombinant EI, EI variants or portions of EI can be achieved by attaching the recombinant compound to antibodies or portions of antibodies, which are directed to an antigen located at a particular physiological site. Additionally, such recombinant variants, derivatives or portions of EI can be attached to insoluble substrates for facilitating the separation of elastase or other Serpin molecules from a solution by performing a chromatographic separation based on specific affinity of the insoluble recombinant EI variant for the Serpin molecule. Such affinity methods are useful for research applications, large scale production and isolation of the soluble molecule and are potentially useful for therapeutic applications (e.g. plasmaphoresis).

Likewise, oligonucleotides complementary to ribonucleotides encoding Human EI or a portion thereof can be useful for some of the above-noted diagnostic purposes. Further, the oligonucleotides encoding Human EI or a portion, derivative or variation thereof, alone or as part of a suitable expression vector or delivery system can be useful in gene replacement therapy relating to the conditions described above. Preparations containing effective amounts of such oligonucleotides, suitable expression vectors or delivery systems are made using conventional cloning and isolation techniques as described above or by other methods such as PCR (polymerase chain reaction). These and many other uses will be apparent to one of ordinary skill in the art.

The foregoing description is intended to be taken in an illustrative, and not a limiting, sense.

References (1) Janoff, A., Blodin, J., "Inhibition of the Elastase-Like Esterase in Human Leukocyte Granules by Human Leukocyte Cell Sap." *Proc. Soc. Exp. Biol. Med.*, 1971, 136:1050–1053.

(2) Blodin, J., Rosenberg, R., Janoff, A., "An Inhibitor in Human Lung Macrophages Active Against Human Neutrophil Elastase." *Am. Rev. Resp. Dis.*, 972, 106:477–479.

(3) Dubin, A., "A Polyvalant Proteinase Inhibitor from Horse-Blood-Leucocyte Cytosol." *Eur. J. Biochem,* 1977. 73:429–435.

(4) Potempa, J., Dubin, A., Travis, J., "An Elastase Inhibitor From Equine Leukocyte Cytosol Belongs to the Setpin Superfamily." *J. Biol, Chem,* 988, 263:7364.

(5) Kopitar, M. and M. Bozic, "Pig Leukocyte Elastase Inhibitor." *Acta Pharm. Jugosl.,* 1985, 35:203–212.

(6) Valentine, R., Goettlich-Riemann, W., Fisher, G. and Rucker, R. B., "An Elastase Inhibitor from Isolated Bovine Pulmonary Macrophages." *Proc. Soc. Exp. Biol. Med.*, 1981, 168: 238–244.

(7) Remold-O'Donnell, E. and K. Lewandrowski, "Two Proteinase Inhibitors Associated with Peritoneal Macrophages." *J. Biol. Chem.*, 1983, 258:3251–3257.

(8) Remold-O'Donnell, E., "A Fast-Acting Elastase Inhibitor in Human Monocytes." *J. Exp. Med.*, 1985, 162:2142–2155.

(9) Sundstrom, C. and Nilsson, K. "Establishment and Characterization of a Human Histiocytic Lymphoma Cell Line (U-937)." *Int. J. Cancer*, 1976, 17: 565–577.

(10) Lazardes, E and Lindberg, U. "Actin is the naturally occurring inhibitor of deoxyribonuclease I" *Proc. Natl. Acad. Sci. USA*, 1974, Vol. 71, 4742–6.

(11) Weber, K., and Osborn, M, "The Reliability of Molecular Weight Determinations by Dodecyl Sulfate-Polyacrylamide Gel Electrophoresis." *J. Biol. Chem,* 1969, 244:4406–4412.

(12) Senior, R. M., Huebner, P. F. and Pierce, J. A., "Measurement of Elastase Activity by Elastin Agar and Its Use in The Detection of Antitrypsin Deficiency". *J. Lab. Clin. Med.*, 1971, 77:510–6.

(13) Merril, C. R. Goldman, D., Sedman S. A., Ebert, M. H., "Ultrasensitive stain for proteins in polyacrylamide gels shows regional variations in cerebrospinal fluid proteins", *Science,* 1981, Vol. 211, 1437–8.

(14) Hirs, C. H. W., *J. Biol. Chem,* 1956, 219:611 and Moore, S., *J. Biol. Chem.,* 1963, 238:235.

(15) Reinhold, V.N., *Methods Enzymol,* 1972, 25:244–249.

(16) Tarentino, A. L., Gomez, C. M., Plummer, T. H., Jr., "Deglycosylation of Asparagine-Linked Glycans by Peptide:N-glycosidase F." *Biochemistry,* 1985, 24:4665–4671.

---

What is claimed is:

1. A method for isolating the gene for Human monocyte elastase inhibior comprising using at least one detection probe constructed and arranged so as to be useful for screenign a library, the detection probe containing an oligonucleotide encodiing a peptide selected from the group consisting of Sequence I.D. Numbers 1 through 11.

2. An isolated and purified DNA comprising oligonucleotide sequence I.D. No. 12.

* * * * *